(12) United States Patent
Palmer et al.

(10) Patent No.: US 11,806,008 B2
(45) Date of Patent: Nov. 7, 2023

(54) DEVICES FOR GENERATING AND APPLYING COMPRESSION WITHIN A BODY

(71) Applicant: Arthrex, Inc., Naples, FL (US)

(72) Inventors: Matthew Palmer, Cambridge, MA (US); Matthew Fonte, Concord, MA (US); Robert Devaney, Auburndale, MA (US); Daniel Morgan, Salem, MA (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 17/896,776

(22) Filed: Aug. 26, 2022

(65) Prior Publication Data

US 2023/0000488 A1    Jan. 5, 2023

Related U.S. Application Data

(63) Continuation of application No. 15/451,711, filed on Mar. 7, 2017, now Pat. No. 11,426,158.

(Continued)

(51) Int. Cl.
*A61B 17/064*    (2006.01)
*A61B 17/068*    (2006.01)
(Continued)

(52) U.S. Cl.
CPC ........ *A61B 17/0642* (2013.01); *A61B 17/068* (2013.01); *A61B 17/0682* (2013.01); *A61B 17/10* (2013.01); *A61B 17/86* (2013.01); *A61B 17/866* (2013.01); *A61B 17/8685* (2013.01); *A61B 17/864* (2013.01); *A61B 2017/00862* (2013.01); *A61B 2017/00867* (2013.01);
(Continued)

(58) Field of Classification Search
CPC .. A61B 17/0642; A61B 17/0682; A61B 17/10
See application file for complete search history.

(56) References Cited

U.S. PATENT DOCUMENTS 9,907,551 B2 *    3/2018  Seavey ............... A61B 17/16
2002/0111641 A1    8/2002  Peterson et al.
(Continued)

FOREIGN PATENT DOCUMENTS

EP        3056154 A1      8/2016
WO    2006/110738 A2    10/2006
(Continued)

OTHER PUBLICATIONS

International Preliminary Report on Patentability for Application No. PCT/US2017/021055 dated Sep. 20, 2018.
(Continued)

*Primary Examiner* — Si Ming Ku
(74) *Attorney, Agent, or Firm* — Carlson, Gaskey & Olds, P.C.

(57) ABSTRACT

This disclosure is directed to surgical fixation devices (e.g., staples, screws, etc.) which are able to bring bone fragments into close proximity with each other, generate a compressive load, and maintain that compressive load for a prolonged period of time while healing occurs. The surgical fixations devices are manufactured from a shape memory material (e.g., a material capable of exhibiting superelasticity and/or a temperature-induced shape change).

14 Claims, 48 Drawing Sheets

Related U.S. Application Data

(60) Provisional application No. 62/361,212, filed on Jul. 12, 2016, provisional application No. 62/349,759, filed on Jun. 14, 2016, provisional application No. 62/304,457, filed on Mar. 7, 2016.

(51) Int. Cl.
*A61B 17/10* (2006.01)
*A61B 17/86* (2006.01)
*A61B 17/00* (2006.01)
*A61B 17/68* (2006.01)

(52) U.S. Cl.
CPC ............... *A61B 2017/00946* (2013.01); *A61B 2017/0645* (2013.01); *A61B 2017/681* (2013.01)

(56) References Cited

U.S. PATENT DOCUMENTS

| | | |
|---|---|---|
| 2005/0277940 A1 | 12/2005 | Neff |
| 2006/0247681 A1 | 11/2006 | De Canniere et al. |
| 2015/0133940 A1 | 5/2015 | Palmer et al. |
| 2015/0313592 A1 | 11/2015 | Coillard-Lavirotte et al. |
| 2016/0235460 A1 | 8/2016 | Wahl |
| 2016/0338697 A1* | 11/2016 | Biedermann ........ A61B 17/064 |
| 2017/0000482 A1 | 1/2017 | Averous et al. |

FOREIGN PATENT DOCUMENTS

| | | |
|---|---|---|
| WO | 2015/070257 A1 | 5/2015 |
| WO | 2015107311 A1 | 7/2015 |
| WO | 2016154417 A1 | 9/2016 |

OTHER PUBLICATIONS

International Search Report and Written Opinion of the International Searching Authority for International application No. PCT/US2017/021055 dated Oct. 9, 2017.

* cited by examiner

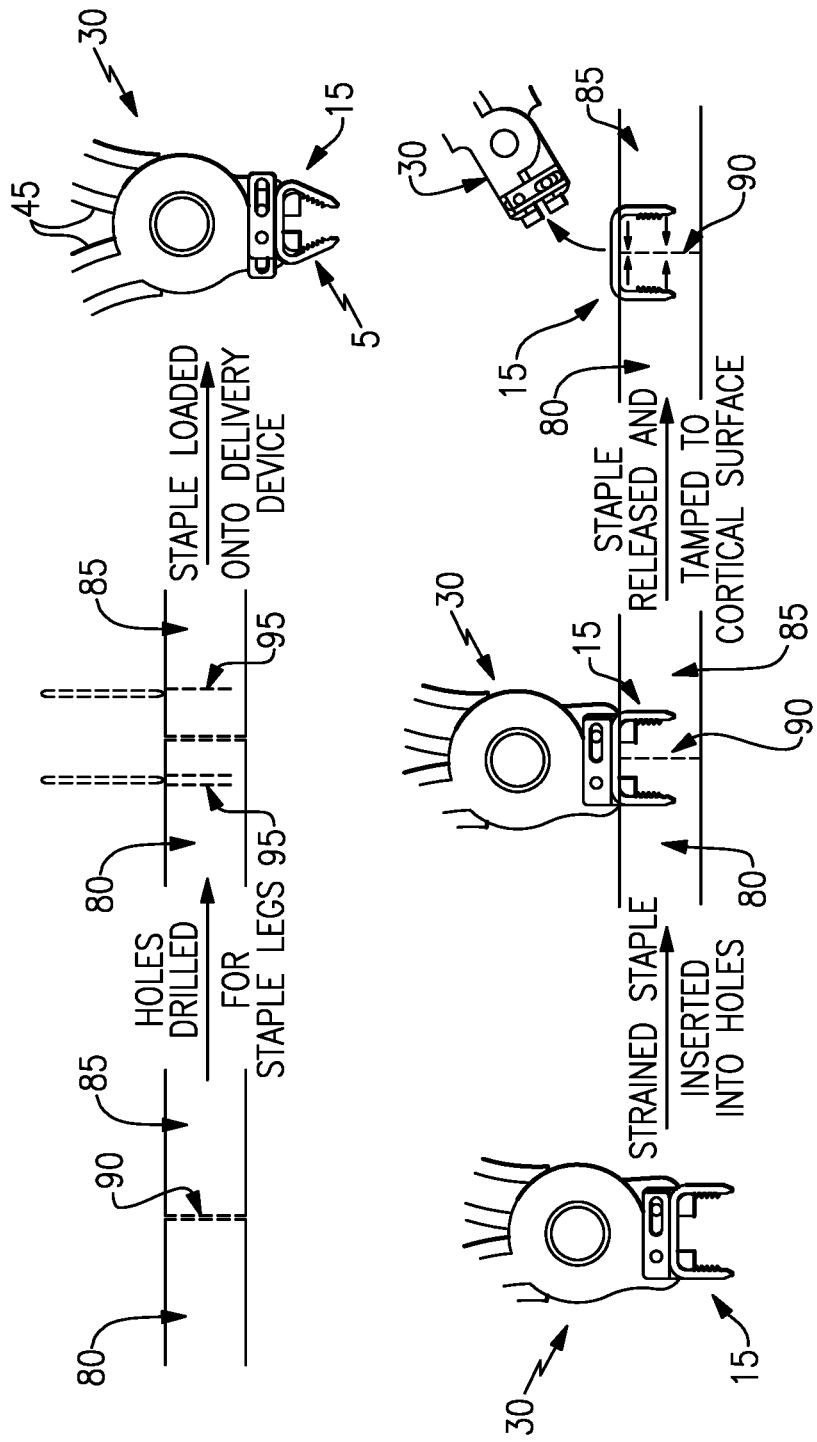

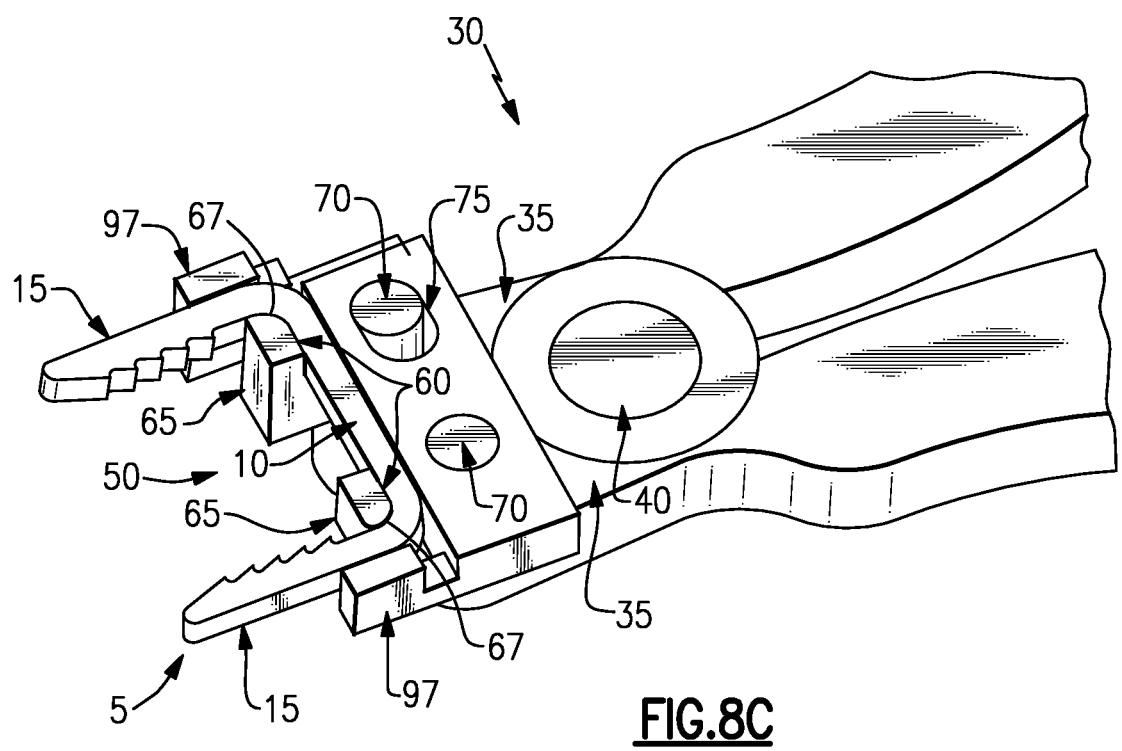

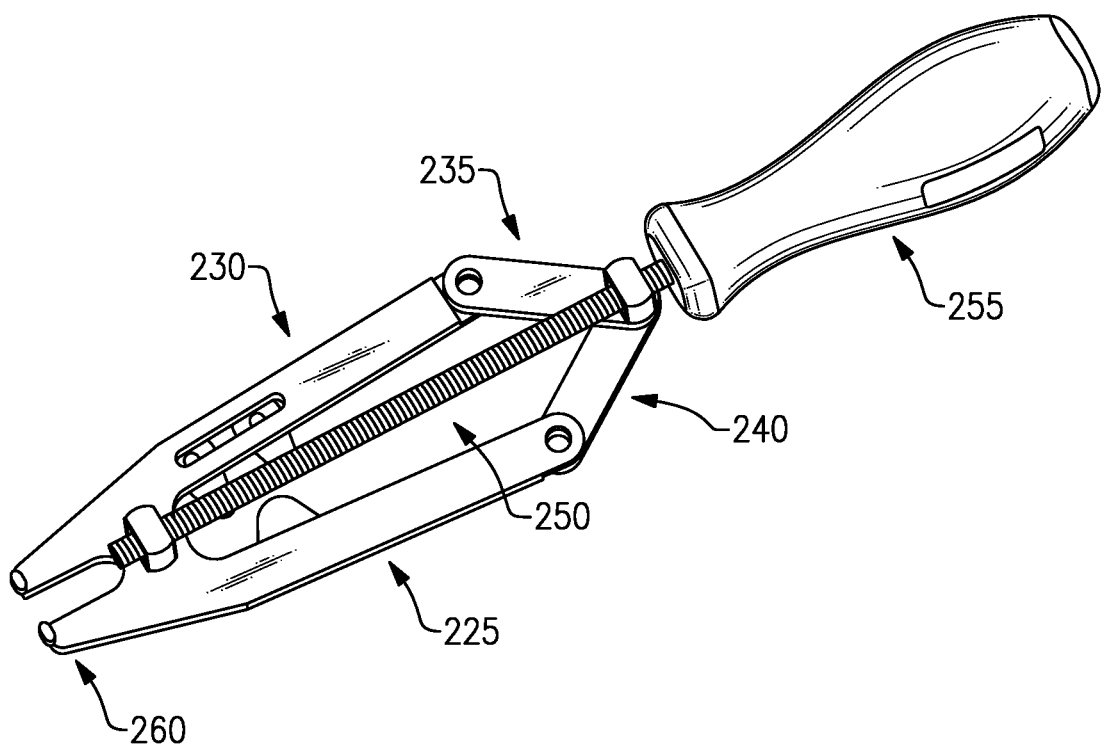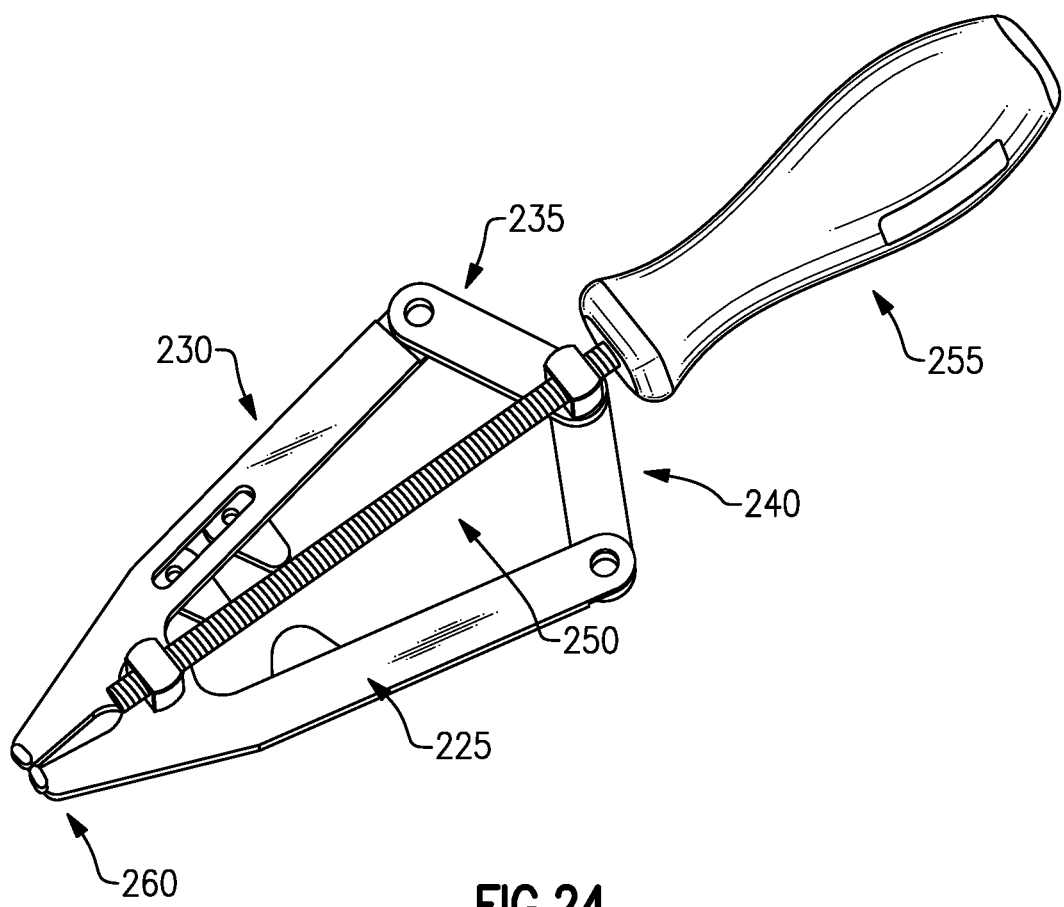
FIG.24

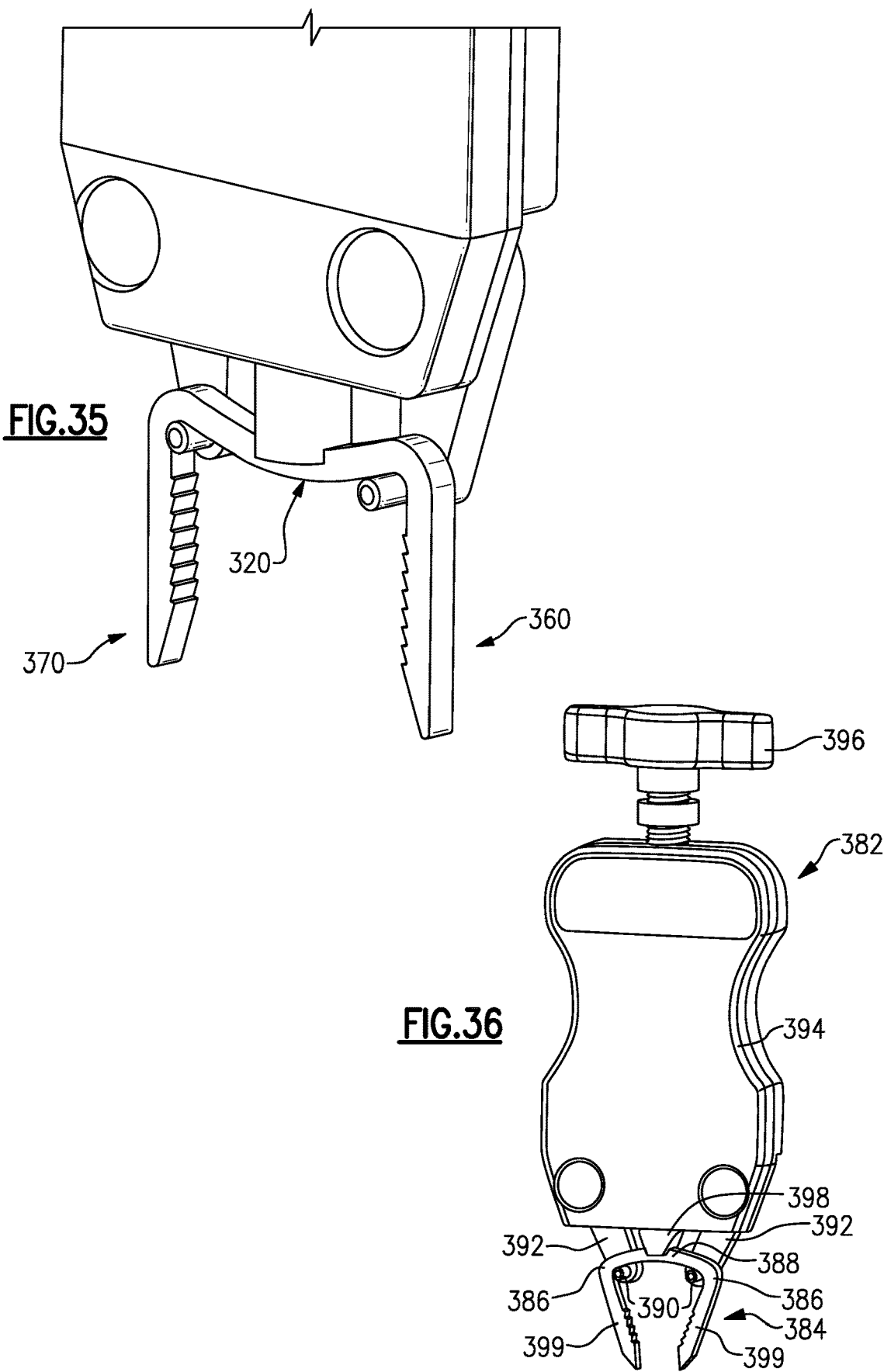

US 11,806,008 B2

DEVICES FOR GENERATING AND APPLYING COMPRESSION WITHIN A BODY

CROSS-REFERENCE TO RELATED APPLICATIONS

This application is a continuation of U.S. patent application Ser. No. 15/451,711 filed Mar. 7, 2017, now U.S. Pat. No. 11,426,158 granted Aug. 30, 2022; which claims priority to U.S. Provisional Application No. 62/304,457 filed on Mar. 7, 2016; and claims priority to U.S. Provisional Application No. 62/361,212 filed on Jul. 12, 2016; and claims priority to U.S. Provisional Application No. 62/349,759 filed on Jun. 14, 2016. The disclosures of each of these prior applications are incorporated herein by reference in their entirety.

TECHNICAL FIELD

This disclosure relates to fixation devices (e.g., stapes, screws, etc.) for generating, applying, and maintaining compression to a site in a human or animal body in order to facilitate healing of diseased or damaged tissue. This disclosure finds particular utility in the field of orthopedics and specifically for reducing fractures and maintaining compression between bone fragments, and/or for reducing openings and maintaining compression between bone segments in osteotomies, and/or for inducing fusion across the bones of a joint in an arthrodesis. While the disclosure has application throughout the body, its utility will be illustrated herein in the context of the repair of fractured or displaced bone tissue, such as during an Akin Osteotomy of the foot or an Isolated Lunocapitate Arthrodesis of the hand/wrist, and in the context of stabilizing the spine as an aid to fusion through bilateral immobilization of the facet joints.

BACKGROUND

In the field of orthopedic surgery, it is common to rejoin broken bones. The success of the surgical procedure often depends on the ability to reapproximate the fractured bones, the amount of compression achieved between the bone fragments, and the ability to sustain that compression over a period of time. If the surgeon is unable to bring the bone fragments into close contact, a gap will exist between the bone fragments and the bone tissue will need to fill that gap before complete healing can take place. Furthermore, gaps between bone fragments that are too large allow motion to occur between the bone fragments, disrupting the healing tissue and thus slowing the healing process. Optimal healing requires that the bone fragments be in close contact with each other, and for a compressive load to be applied and maintained between the bone fragments. Compressive strain between bone fragments has been found to accelerate the healing process in accordance with Wolf's Law.

Broken bones can be rejoined using staples. Staples are formed from a plurality of legs (typically two legs, though sometimes more) connected together by a bridge. Staples are typically manufactured from either stainless steel alloys, titanium alloys or Nitinol, a shape memory alloy. The staples are inserted into pre-drilled holes on either side of the fracture site, with the bridge of the staple spanning the fracture line.

While these staples are designed to bring the bone fragments into close contact and to generate a compressive load between the bone fragments, the staples do not always succeed in accomplishing this objective. It is widely reported that the compressive load of staples dissipates rapidly as the bone relaxes and remodels around the legs of the staples. Furthermore, current staple systems do not allow the surgeon to control the amount of compression that the staple will exert when it is released from the delivery device, do not allow the surgeon to control the rate at which the staple loads the bone when it is removed from the delivery device, and do not allow the surgeon to control the extent to which the staple's legs are opened.

Thus there exists a clinical need for fixation devices that are able to bring bone fragments into close proximity with each other, generate a compressive load, and maintain that compressive load for a prolonged period of time while healing occurs.

Moreover, existing staples have bridges that are fixed in size, shape, and dimension, while each procedure presents a unique anatomical requirement (which is set by a combination of indication and patient-specific anatomy). Existing staples with fixed shape and dimension bridges will often sit "proud" of the cortical bone, resulting in irritated and inflamed adjacent soft tissue and, in some cases, bursitis.

Thus there also exists a clinical need for a staple with a malleable bridge that may be bent so as to conform to the unique anatomical structure of each patient and sit flush on the cortical surface of the bone.

Moreover, in the field of spine surgery, it is common to fuse adjacent vertebra. Facet fixation screws are commonly used to induce fusion. The screws are intended to stabilize the spine as an aid to fusion through bilateral immobilization of the facet joints. For transfacet fixation, the screws are inserted through the inferior articular process across the facet joint and into the pedicle. For translaminar facet fixation, the screws are inserted through the lateral aspect of the spinous process, through the lamina, through the inferior articular process, across the facet joint and into the pedicle. The current invention disclosed herein may be utilized for bilateral facet fixation, with or without bone graft, at single or multiple levels from C2 to S1 inclusive.

Thus there further exists a clinical need for fixation devices that are able to bring adjacent vertebra into close proximity with each other, generate a compressive load, and maintain that compressive load for a prolonged period of time while fusion occurs.

SUMMARY

This disclosure provides novel fixation devices (e.g., staples, screws, etc.) which are able to bring bone fragments into close proximity with each other, generate a compressive load, and maintain that compressive load for a prolonged period of time while healing occurs.

Among other things, this disclosure includes the provision and use of a novel monolithic staple which is manufactured from a single piece of shape memory material (e.g., a material capable of exhibiting superelasticity and/or a temperature-induced shape change). The shape memory material may be a metal alloy (e.g., Nitinol) or a polymer (e.g., appropriately processed PEEK). The staple is designed to reduce fractures and generate and maintain more uniform compression between the cortical bone and cancellous bone of the bone fragments to aid in fracture healing.

In an embodiment, a staple includes an elastic bridge and two elastic legs. The bridge and the legs meet at a pair of curved hinge regions which are also elastic. In the unrestrained state, the legs of the staple are bent inward with an angle of less than 90°. Prior to implantation, the bridge of the staple can be reversibly strained outward (i.e., stretched longitudinally outward) and the legs of the staple can be reversibly bent to a position perpendicular to the longitudinal axis of the bridge so as to allow for insertion of the staple into a prepared fracture site. A delivery device may be used to strain the bridge, bend the legs to parallel, hold the staple in this strained state prior to implantation, and insert the strained staple into the prepared fracture site. When the constraint on the bridge and legs is removed, the bridge and legs attempt to return to their original unrestrained state, thereby generating a greater, and more uniform, compressive load and maintaining that greater, and more uniform, compressive load for a prolonged period of time while healing occurs.

In another embodiment, a staple includes a malleable bridge and two elastic legs. The bridge and the legs meet at a pair of curved hinge regions which are also elastic. In the unrestrained state, the legs of the staple are bent inward with an angle of less than 90°. Prior to implantation, the malleable bridge may be deformed so that it conforms to the unique anatomical structure of the patient, such that it will sit flush with the cortical surface of the bone after implantation. And prior to implantation, the legs of the staple can be reversibly bent to a position perpendicular to the longitudinal axis of the bridge so as to allow for insertion of the staple into a prepared fracture site. A bending device may be used to deform the bridge, and a delivery device may be used to hold the deformed bridge, bend the legs, hold the staple in this state prior to implantation, and insert the staple into the bone, with the bridge of the staple extending across the fracture line. Alternatively, a combined bending/delivery device may be used to deform the bridge, bend the legs, hold the staple in this condition prior to implantation, and insert the staple into the bone, with the bridge of the staple extending across the fracture line. Upon insertion of the deformed and strained staple into the prepared fracture site, the constraint on the legs of the staple is removed, whereupon the legs of the staple attempt to return to their original unrestrained state, thereby generating a compressive load and maintaining that compressive load for a prolonged period of time while healing occurs. Significantly, the deformed bridge of the staple can be matched to the unique anatomical structure of the patient, such that the bridge of the staple will sit flush with the cortical surface of the bone.

Additionally, it is possible that where the staple comprises a malleable bridge with two elastic legs, the staple can be inserted into the fracture site prior to bending the bridge. The bridge can be bent after implantation using a tamp-like device of the sort known in the art.

In another embodiment, a surgical system includes a delivery device and a staple. The delivery device may engage the staple underneath a bridge of the staple. The delivery device may be actuated to deform the staple bridge such that staple legs are substantially parallel to each other for insertion into prepared bone holes. Releasing the staple from the delivery device allows the staple legs to re-assume a convergent position.

In another embodiment, a compression screw is manufactured from a shape memory material (e.g., a material capable of exhibiting superelasticity and/or a temperature-induced shape change). The shape memory material may be a metal alloy (e.g., Nitinol) or a polymer (e.g., appropriately processed PEEK). The compression screw is designed to engage bones and to generate compression between the bones. The compression screw has an enlarged head and a distal threaded region. The head is connected to the threaded region by a hollow central bridge region. The hollow central bridge region can be strained and reversibly elongated, e.g., up to about 8% where the compression screw is formed from Nitinol. The hollow central bridge region may be strained and reversibly elongated prior to implantation by releasing that strain after implantation of the compression screw across the fusion line. The contracting hollow central bridge region can aid in approximating and provide additional therapeutic compression to the bones, whereby to provide superior fusion.

In another embodiment, a screw is inserted through an optional washer. The hole in the washer is sized so as to allow the distal threads to pass through, but not to allow the enlarged head to pass through. This allows for a large surface area for the screw to distribute its compressive force over. Furthermore, the enlarged head can articulate in the washer, allowing the screw to be inserted at an angle, but still have the washer shit flush with the bone surface.

In another embodiment, a compression screw system includes a compression screw having a shaft, a screw thread formed on the shaft at a distal location, and an enlarged head formed on the shaft at a proximal location. At least a portion of the shaft disposed between the screw thread and the enlarged head feature is capable of being stretched. A holding element is connectable to the compression screw for releasably holding the portion of the shaft in a stretched condition.

In another embodiment, a method for fusing bone longitudinally stretching a compression screw so that the compression screw is in a longitudinally stretched condition, holding the compression screw in its longitudinally stretched condition, inserting the compression screw into bone while the compression screw is in its longitudinally stretched condition so that the compression screw extends across the fusion site, and releasing the compression screw from its longitudinally stretched condition to apply compression across the fusion site.

In yet another embodiment, a compression screw system includes a compression screw having a shaft capable of being stretched. The shaft has a proximal end, a distal end, and a lumen extending therebetween. The proximal end of the shaft includes an enlarged head and the distal end of the shaft includes a distal screw thread. The lumen includes a distal bore, an intermediate counterbore communicating with the distal bore so as to define a first shoulder, and a proximal counterbore communicating with the intermediate counterbore so as to define a second shoulder. The proximal counterbore includes a connection feature and the proximal end of the shaft includes a drive feature for turning the compression screw. An internal retaining pin includes a pin shaft having a proximal end, a distal end, and a lumen extending therebetween. The proximal end of the pin shaft includes a second connection feature configured to mate with the connection feature of the proximal counterbore of the compression screw. The distal end of the pin shaft terminates in a distal end surface. The internal retaining pin includes a pin drive feature for turning the internal retaining pin, and the internal retaining pin is sized such that, when the shaft of the compression screw is stretched, and when the internal retaining pin is inserted into the lumen of the compression screw such that the second connection feature of the internal retaining pin is engaged with the connection feature of the proximal counterbore of the compression screw and contacts the second shoulder of the compression screw, the distal end surface of the pin shaft engages the first shoulder of the compression screw to prevent foreshortening of the stretched compression screw.

BRIEF DESCRIPTION OF THE DRAWINGS

The various features and advantages of this disclosure will become apparent to those skilled in the art from the following detailed description. The drawings that accompany the detailed description can be briefly described as follows.

FIG. 8 is a schematic view showing how the novel staple of FIG. 1 may be used to generate and maintain a greater, and more uniform, compression between bone fragments so as to aid in fracture healing.

FIGS. 8A, 8B, and 8C are schematic views showing another form of a delivery device which may be used with the novel staple shown in FIG. 1 to elastically strain (i.e., stretch) the bridge of the staple and elastically bend the legs of the staple.

FIG. 9 shows the staple in its unstrained condition and FIG. 10 shows the staple with its bridge bent but its legs in an unstrained condition.

FIGS. 22, 23, 24, 25, 26, 27, and 28 are schematic views of another novel device which may be used to bend the bridge of the staple shown in FIG. 10A and also bend the staple legs to substantially parallel and implant the staple across the fracture site.

FIGS. 34 and 35 schematically illustrate the use of a delivery device of a surgical system for deforming a staple bridge to a concave state.

FIGS. 36 and 37 illustrate another exemplary surgical system that includes a delivery device and a staple.

DETAILED DESCRIPTION

Figure 1:
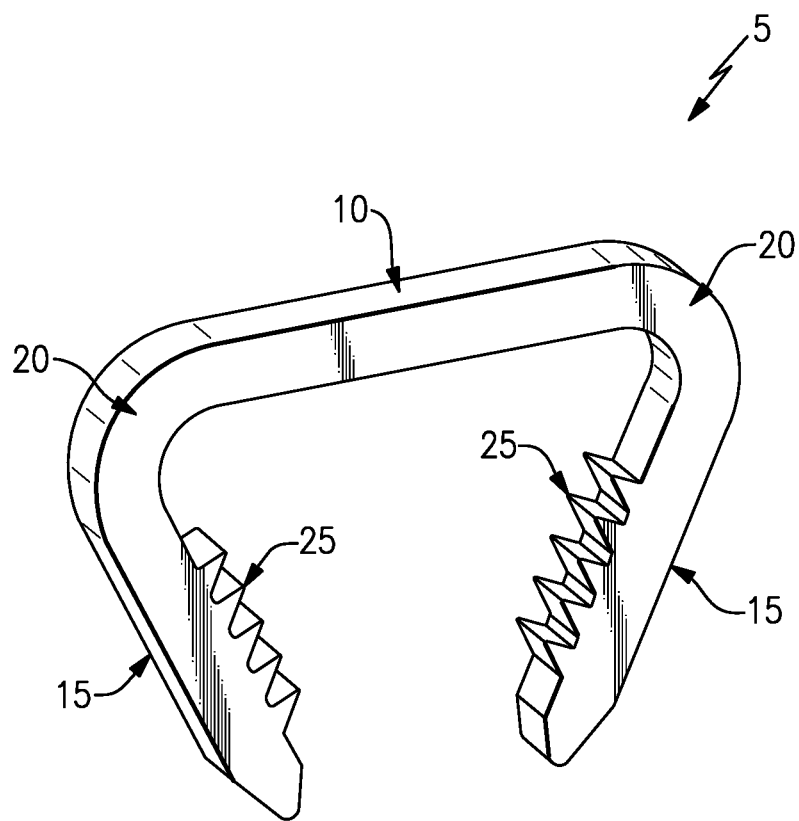
FIG. 1 is a schematic view of a novel staple formed in accordance with the present disclosure. The staple includes a bridge capable of being elastically strained and legs which are capable of being elastically strained. The staple is shown in an unstrained condition.

An exemplary staple includes a bridge, a first leg connected to the bridge and configured to be elastically deformable, and a second leg connected to the bridge and configured to be elastically deformable. The first leg and the second leg are movable between an unrestrained state in which the first leg and the second leg converge toward one another and a constrained state in which the first leg and the second leg are moved toward a parallel position when a force is applied to at least one of the bridge or the first leg and the second leg.

In a further embodiment, a bridge of a staple is elastically deformable and superelastic.

In a further embodiment, a bridge of a staple is malleable and non-superelastic.

In a further embodiment, a bridge, a first leg, and a second leg of a staple are integrally formed out of a single piece of shape memory material to establish a monolithic structure.

In a further embodiment, a shape memory material used to form a staple includes PEEK or Nitinol.

In a further embodiment, a first leg of a staple is connected to a bridge by a first hinge and a second leg is connected to the bridge by a second hinge, and the first hinge and the second hinge are elastically deformable.

In a further embodiment, a hole is formed through first and second hinges of a staple.

In a further embodiment, a bridge of a staple is convex in an unrestrained state of the staple.

In a further embodiment, each of a first leg and a second leg of a staple includes a plurality of barbed teeth.

In a further embodiment, a bridge of a staple is stretched longitudinally and legs of the staple are reversibly bent to a position that is substantially perpendicular to the bridge in a constrained state of the staple.

An exemplary surgical system includes a delivery device and a staple mountable to the delivery device. The staple is made of a shape memory material and includes a bridge, a first leg connected to the bridge by a first hinge region, and a second leg connected to the bridge by a second hinge region. The delivery device is adapted to engage the staple either under the bridge or through holes formed in the first hinge region and the second hinge region and is adapted to move the staple from a first position in which the first leg and the second leg are convergent and a second position in which the first leg and the second leg are substantially parallel.

In a further embodiment, a delivery device includes a rotatable knob and a plunger, and rotation of the rotatable knob moves the plunger to deform a bridge of a staple.

In a further embodiment, a delivery device includes pins that engage a staple either under a bridge or through holes formed in the staple.

In a further embodiment, a delivery device includes a staple mount adapted to both longitudinally stretch a bridge and bend first and second legs of a staple.

In a further embodiment, a bridge of a staple is malleable and non-superelastic and a surgical system includes a bending device adapted to bend the bridge of the staple to a desired geometry prior to mounting the staple to a delivery device.

In a further embodiment, a bending device includes a screw mechanism movable to drive a drive element against a bridge of a staple to bend the bridge.

In a further embodiment, a delivery device includes a plier assembly having a straining fixture adapted to hold a first leg and a second leg of a staple in a position.

In a further embodiment, a surgical system includes a combination bending device and delivery device.

In a further embodiment, a combination bending device and delivery device includes a staple holder and an anvil that cooperate to bend a staple and staple grips that cooperate to engage the staple for inserting the staple into bone.

Another exemplary surgical system includes a compression screw and an internal retaining pin. The compression screw includes a shaft, a screw thread formed on a distal region of the shaft, and an enlarged head formed on a proximal region of the shaft. A portion of the shaft disposed between the screw thread and the enlarged head is capable of being stretched to an elongated state. The internal retaining pin is insertable into the compression screw for releasably holding the portion of the shaft in the elongated state.

FIG. 1 illustrates a staple 5 for bringing bone fragments into close proximity with each other, generating a greater, more uniform (i.e., across the cortical bone and the cancellous bone) compressive load across the fracture line, and maintaining that greater, more uniform compressive load for a prolonged period of time while healing occurs.

The staple 5 is preferably an integral, monolithic structure manufactured from a single piece of shape memory material (e.g., a material capable of exhibiting superelasticity and/or a temperature-induced shape change). The shape memory material may be a metal alloy (e.g., Nitinol) or a polymer (e.g., appropriately processed PEEK).

The staple 5 is designed to reduce fractures and generate and maintain greater and more uniform compression between bone fragments to aid in fracture healing. The staple 5 includes an elastic bridge 10 and two elastic legs 15 that extend from the bridge 10. The bridge 10 and the legs 15 meet at a pair of curved hinge regions 20, which are also elastic. The legs 15 may have one or more barbed teeth 25 adapted to grip into the bone after implantation and prevent the legs of the staple from working their way back out of the bone. In an un-restrained state, the legs 15 of the staple 5 are bent inward with an angle of less than 90°. In an embodiment, the legs 15 extend at an angle of about 45° to the longitudinal axis of the bridge 10 when in their unrestrained state.

Figure 2:
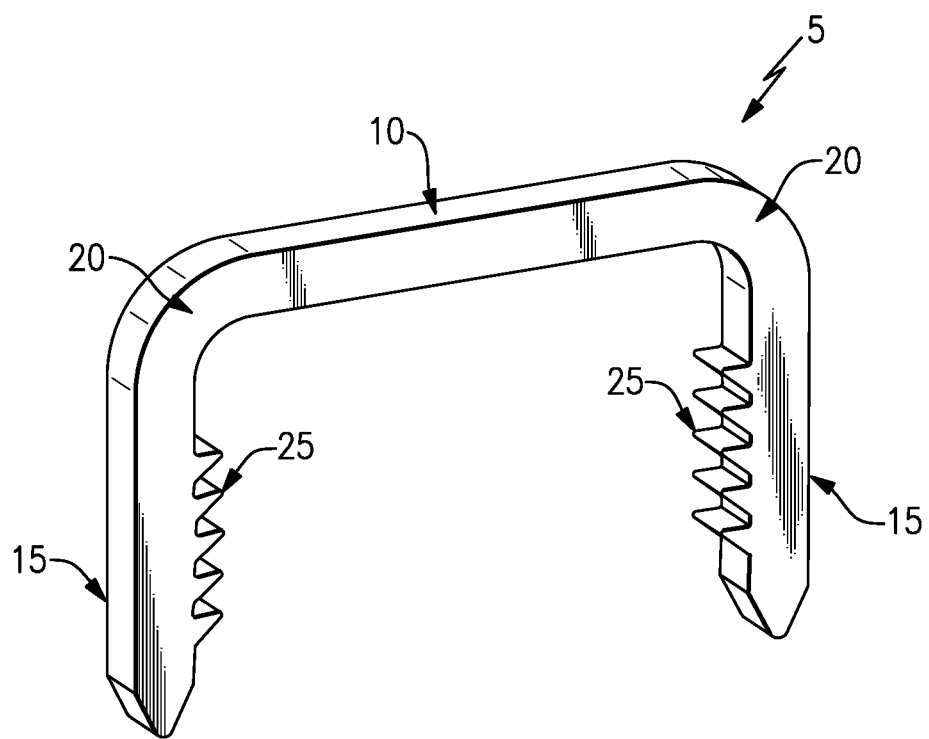
FIG. 2 is a schematic view of the novel staple shown in FIG. 1. The bridge of the staple has been elastically strained (i.e., longitudinally stretched) and the legs of the staple have been elastically bent outwards.

Prior to implantation, the bridge 10 of the staple 5 can be reversibly strained outward (i.e., stretched longitudinally) and the legs 15 of staple 5 can be reversibly bent to a position substantially perpendicular to bridge 10 (see FIG. 2) so as to allow for insertion of the legs of the staple 5 into a prepared fracture site. Once implanted, the stretched bridge 10 of the staple 5 spans across the fracture line. In an embodiment where the staple 5 is formed out of Nitinol, elastic deformations of up to approximately 8% are achievable. A delivery device (described below) can be used to strain the bridge 10 and bend the legs 15, hold the staple 5 in this strained state prior to implantation, and then insert the staple 5 into the prepared fracture site.

Figure 3:
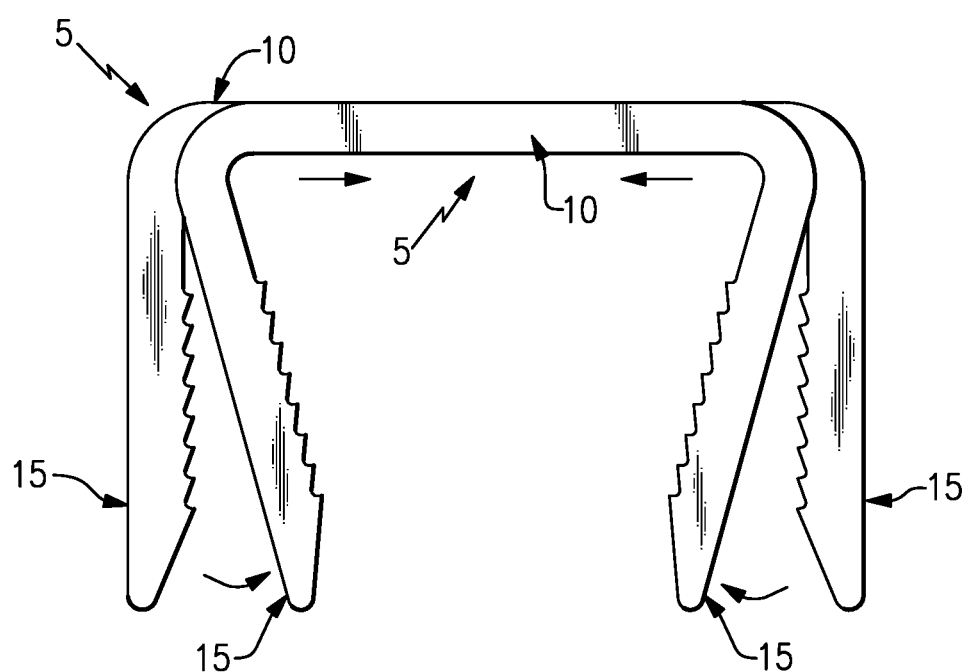
FIG. 3 is a schematic view showing how the elastically strained staple of FIG. 2 will foreshorten along its bridge and have its legs "kick inward." The strain on the staple is removed.
Figure 4:
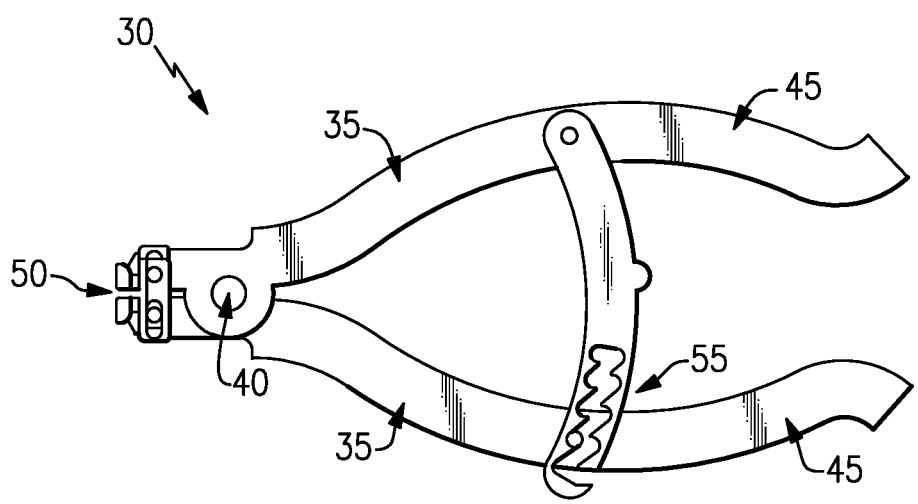
FIGS. 4 and 5 are schematic views showing an exemplary delivery device which may be used with the novel staple shown in FIG. 1 to elastically strain (i.e., stretch) the bridge of the staple and elastically bend the legs of the staple.

Upon insertion of the strained staple 5 into the prepared fracture site, the constraint on bridge 10 and the legs 15 is removed, whereupon the staple 5 attempts to return to its original un-restrained state (see FIG. 3), thereby generating a greater compressive load with more uniformity along the fracture line (i.e., through the legs 15 and the compressive bridge 10), and maintaining that compressive load for a prolonged period of time while healing occurs.

Referring next to FIGS. 4-7, an exemplary delivery device 30 which may be used to strain (i.e., stretch) the bridge 10 and bend the legs 15 of the staple 5. The delivery device 30 includes two arms 35 which are pivotally connected together at a pivot pin 40, a pair of handles 45 on one end for actuating the delivery device 30, and a staple mount 50 on the other end for holding and straining the staple 5. When the staple 5 is mounted to the staple mount 50 of the delivery device 30 and the handles 45 are thereafter moved toward one another, the staple mount 50 translates apart, thus stretching the bridge 10 of the staple 5 and bending legs 15 of the staple 5 outward to a position substantially perpendicular to the longitudinal axis of the bridge 10. The delivery device 30 includes a locking feature 55 that facilitates holding the staple 5 in its strained state and allows for easy insertion of the staple 5 into a prepared fracture site. The locking feature 55 may be configured so that the surgeon can strain the staple to different degrees, thereby (i) enabling the surgeon to tailor the compressive force (e.g., by bending only legs 15, or by bending legs 15 and straining bridge 10), and (ii) enabling the surgeon to tailor the amount of recoverable strain established across the fracture line (e.g., by varying the amount that bridge 10 is stretched), depending on bone quality.

Figure 5:
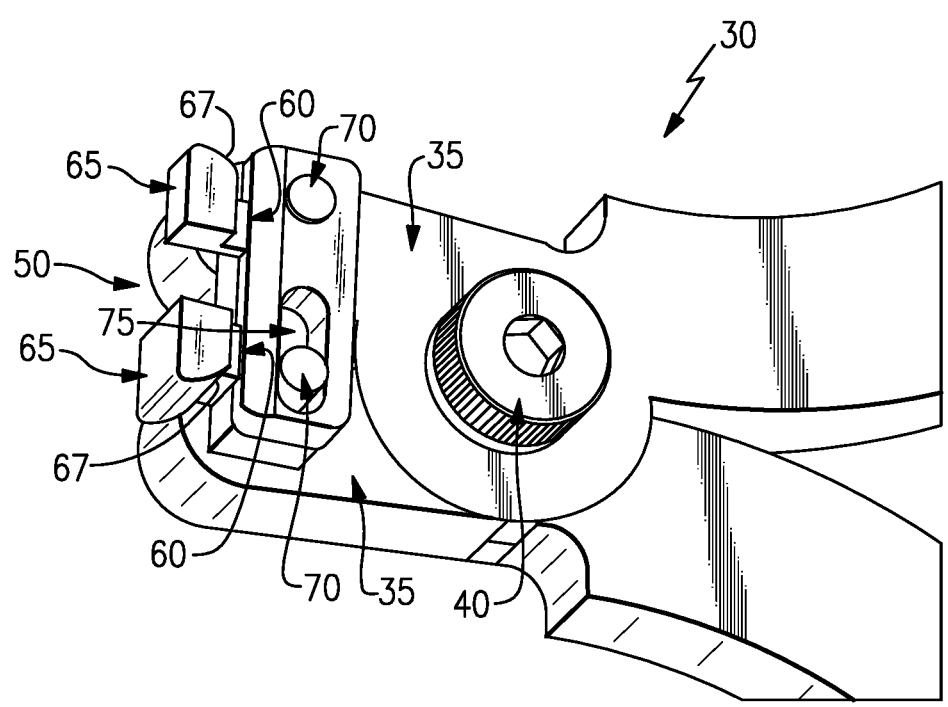

FIG. 5 shows a close-up of the staple mount 50 of the delivery device 30. The staple mount 50 includes a channel 60 that receives the bridge 10 of staple 5 and two staple-stretching linkages 65 which sit distal to, and help define, the channel 60. Radii 67 of the staple-stretching linkages 65 mate with the curved hinge regions 20 of the staple 5 when the legs 15 of the staple have been strained (i.e., bent) outward to a position substantially perpendicular to the longitudinal axis of the bridge 10. Each staple-stretching linkage 65 is connected to the arms 35 by a pin 70. The pins 70 slide in channels 75 provided on the staple-stretching linkages 65 (i.e., a first pin 70 mounted to a first staple-stretching linkage 65 slides in a channel 75 of the second staple-stretching linkage 65, and a second pin 70 mounted to the second staple-stretching linkage 65 slides in the channel 75 of the first staple-stretching linkage 65). The channels 75 are sized to limit the maximum amount of strain that may be imposed on the bridge 10 of staple 5 by the delivery device 30 (i.e., the channels 75 limit the extent to which bridge 10 of staple 5 may be stretched).

Figure 6:
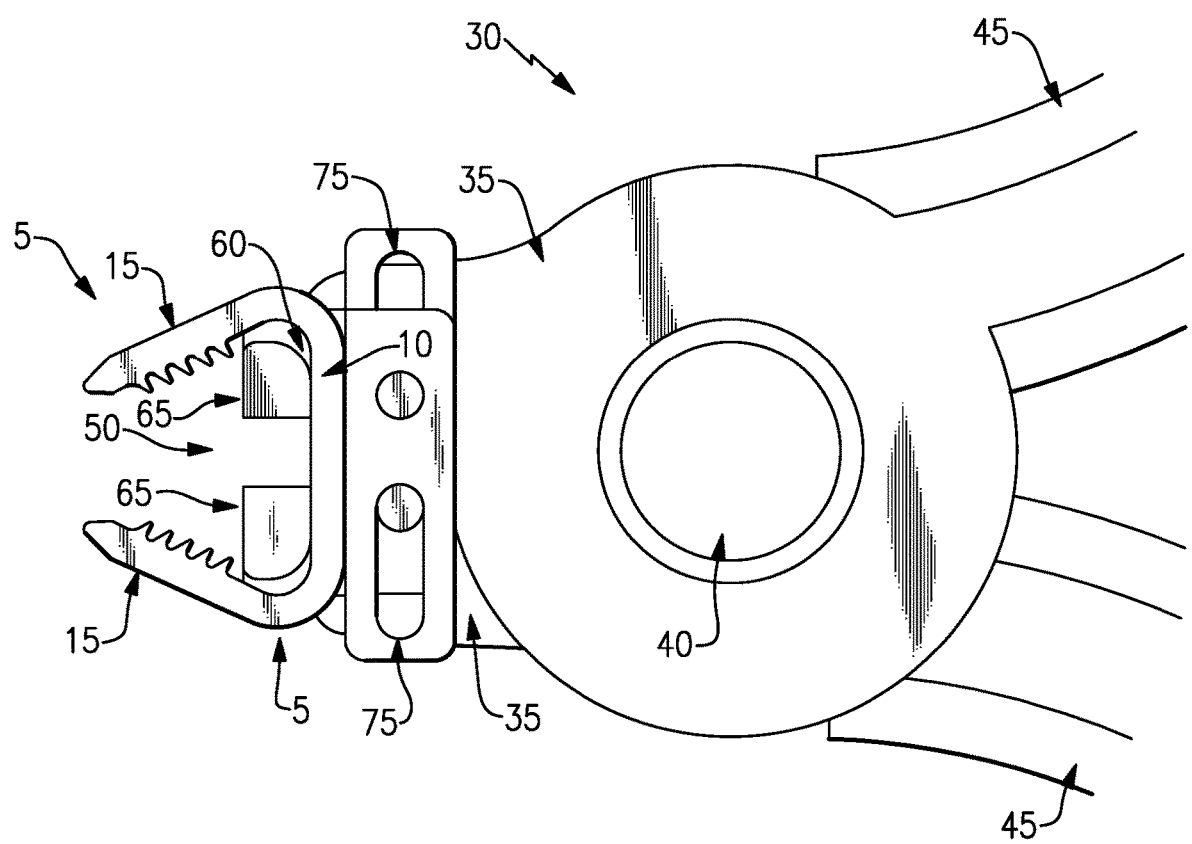
FIGS. 6 and 7 are schematic views showing the delivery device of FIGS. 4 and 5 being used with the novel staple shown in FIG. 1 to elastically strain (i.e., stretch) the bridge of the staple and elastically bend the legs of the staple.
Figure 7:
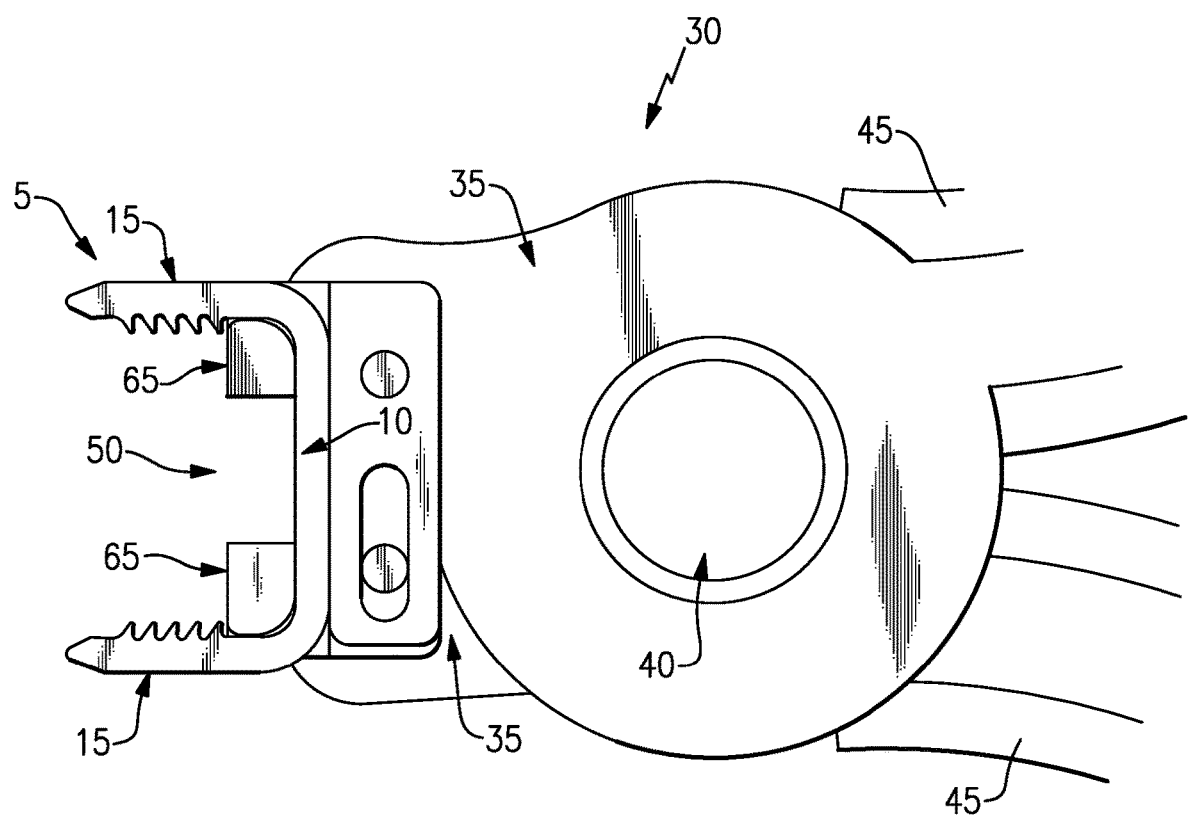

FIGS. 6 and 7 show the staple 5 being loaded onto the delivery device 30 and the staple 5 being strained, i.e., bridge 10 being stretched and legs 15 being bent so that they are perpendicular to the longitudinal axis of bridge 10. More particularly, FIG. 6 shows the staple 5 loaded onto the staple mount 50 of the delivery device 30 while the staple mount 50 of the delivery device 30 is in its closed (i.e., non-staple-straining) position. This is done by positioning the bridge 10 of staple 5 in the channel 60 of the staple mount 50. In this position, the legs 15 of the staple 5 are in their unbiased, converging position. FIG. 7 shows the staple 5 after the handles 45 of the delivery device 30 have been moved together, so that the staple mount 50 is in its open (i.e., staple-straining) position. This is done by moving handles 45 of delivery device 30 together, thereby forcing staple-stretching linkages 65 of staple mount 50 apart, and causing bridge 10 of staple 5 to be stretched and causing legs 15 of staple 5 to be positioned substantially perpendicular to the longitudinal axis of bridge 10.

In an embodiment, the delivery device 30 is constructed so that upon squeezing the handles 45, the legs 15 of the staple 5 are first bent to perpendicular and then, when the legs 15 of the staple 5 are substantially perpendicular, the bridge 10 of the staple 5 is elongated.

In another embodiment, the staple 5 is configured so that the force that is generated as the staple 5 reconfigures (i.e., as the bridge 10 foreshortens and the legs 15 bend inward) is less than the "tear through" force of the bone receiving legs 15, i.e., staple 5 is specifically engineered so as to not "tear through" the bone tissue when attempting to reconfigure. The delivery device 30 may include the aforementioned locking feature 55 which enables the surgeon to control the extent to which the staple 5 is strained (e.g., to bend only the legs of the staple, or to both bend the legs of the staple and strain the bridge of the staple, and to control the extent to which the bridge is stretched), thereby allowing the surgeon to tailor the compressive forces and recoverable strain imposed on the anatomy, depending on bone quality. The compressive forces of the staple 5 can be controlled by modulating the material properties of the staple and/or the geometry of the staple.

The percentage of cold work in the shape memory material forming the staple 5 affects the compressive force generated by the reconfiguring staple 5. As the percentage of cold work increases, the compression force declines. In and embodiment, the staple 5 includes between about 15% and 55% cold work to control the recovery force of the staple 5. However, other degrees of cold work may be used, and/or the material may not be cold worked at all.

Another material property that affects the compression force of the staple 5 is the temperature differential between the body that the staple 5 will be implanted into (assumed to be 37° C., which is the temperature of a human body) and the austenite finish temperature of the shape memory material forming staple 5. A smaller temperature differential between the two will result in the staple 5 generating a smaller compressive load; conversely, a larger temperature differential between the two will result in the staple generating a larger compressive load. The shape memory material that the staple 5 is made out of may have an austenite finish temperature of greater than about −10° C., resulting in a temperature differential of about 47° C. when the staple 5 is implanted (assuming that the staple is implanted in a human body).

The geometry of the staple 5 may also affect the compression forces generated. The cross-sectional area of the bridge 10 and the cross-sectional area of the legs 15 affect the compression forces generated by the reconfiguring staple 5. As the cross-sectional areas increase, so do the compression forces that the reconfiguring staple 5 will generate.

The staple legs 15 are critical for transmitting the compression force to the bone without "tearing through" the bone. The height, width, and length of the staple legs 15, and the geometry of the staple legs 15, are all significant relative to the staple's ability to not "tear through" the bone. Staple legs 15 with greater surface area are better able to distribute the compression force and thus not "tear through" the bone.

FIG. 8 schematically illustrates how the staple 5 may be used to reduce a fracture 90 and generate and maintain greater and more uniform compression between bone fragments 80 and 85 to aid in fracture healing. More particularly, the fracture 90 to be fused is first re-approximated and reduced. A drill guide (not shown) of the sort well known in the art is used to drill two holes 95 the correct distance apart to accommodate the legs 15 of the strained staple 5. The staple 5 is loaded onto the delivery device 30, and the delivery device 30 is used to stretch the bridge 10 and straighten the legs 15 of staple 5 (i.e., by squeezing together handles 45). While still on the delivery device 30, the legs 15 of the staple 5 are placed into the pre-drilled holes 95. The staple 5 is then released from the delivery device 30, which allows the stretched bridge 10 of the staple 5 to foreshorten so as to apply compression to the fracture 90, and which allows the strained legs 15 of the staple 5 to "kick in" and thereby apply additional inward pressure across the fracture 90. Thus, the staple 5 applies more uniform compression across the fracture site, generating compression across both the cortical and intramedullary surfaces, using the compressive forces generated by the foreshortening bridge 10 of the strained staple 5 and using the compressive forces generated by the inwardly bending legs 15 of the strained staple 5.

Significantly, when the bridge 10 and the legs 15 of the staple 5 generate a compressive force, both the cortical regions of the bone fragments and the cancellous regions of the bone fragments are pulled together. This provides a superior balance of compression across different regions of the bone.

It should also be appreciated that, if desired, the staple 5 could be used to attach soft tissue to bone (e.g., to attach a rotator cuff to bone).

It should also be appreciated that the delivery device 30 may not always seat the staple 5 with the bridge 10 of the staple 5 seated directly against the cortical surface of the bone (i.e., the bridge 10 may sit slightly above the cortical surface of the bone). Therefore, a tamp of the sort well known in the art may be used to fully seat the staple 5 bridge against the cortical surface of the bone.

In some circumstances it can be desirable to modify the delivery device 30 to ensure that the legs 15 do not be bent past 90 degrees (relative to the longitudinal axis of bridge 10) when the staple 5 is strained. More particularly, in some constructions, the staple 5 can require more force to stretch the bridge 10 than to bend the legs 15. In this circumstance, there is the possibility that legs 15 will be bent to 90 degrees (relative to the longitudinal axis of bridge 10) and then, as bridge 10 is stretched, legs 15 may be bent past 90 degrees (relative to the longitudinal axis of bridge 10). Therefore, it can be desirable to provide means for preventing legs 15 from being bent past 90 degrees (relative to the longitudinal axis of bridge 10).

Figure 8A:
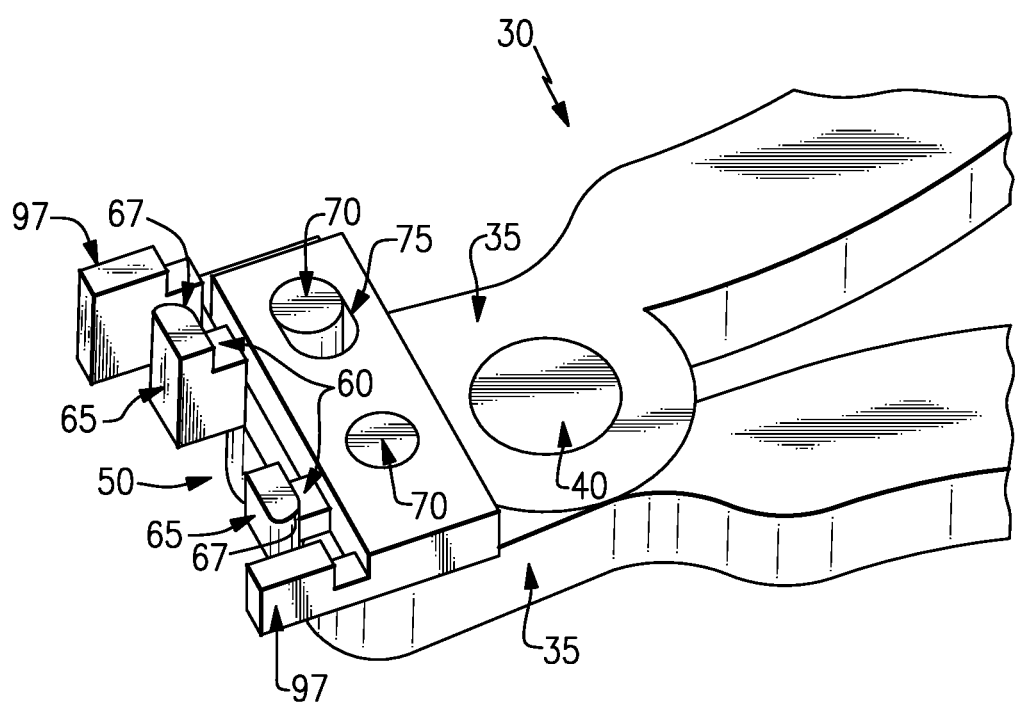
Figure 8B:
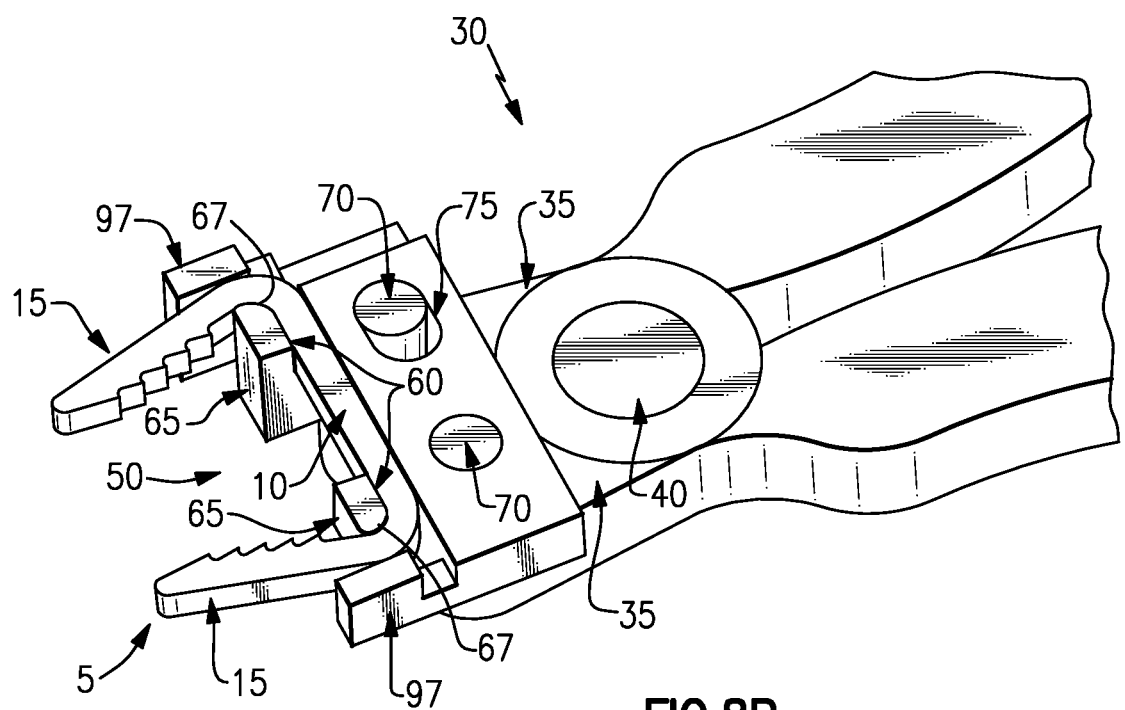

To this end, and looking now at FIGS. 8A, 8B, and 8C, a delivery device 30 may be constructed so that its staple-straining linkages 65 are each formed with an outboard constraint 97 that prevents legs 15 from being bent past 90 degrees (relative to the longitudinal axis of bridge 10) when the staple 5 is strained.

In an embodiment, the staple 5 and delivery device 30 establish a surgical system that is provided in the form of a sterilized kit. The kit may include additional instruments to aid in the implantation of the staple (e.g., k-wire, drill bit, staple size guide, tamp, etc.).

As discussed above, the staple 5 is strained so that, upon deployment in the bone, it will provide compression across a fracture. However, it should also be appreciated that, if desired, the staple 5 could be configured to provide a distraction force to a bone. In this situation, the staple 5 can be configured and strained so that the bridge 10 is compressed, and/or legs 15 can be bent outward, such that when staple 5 is deployed in bone, the reconfiguring staple 5 applies a distraction force to the bone to cause the bone to grow and thereby elongate.

As further discussed above, the staple 5 is manufactured from a shape memory material (e.g., a material capable of exhibiting superelasticity and/or a temperature-induced shape change). The shape memory material may be a metal alloy (e.g., Nitinol) or a polymer (e.g., appropriately processed PEEK). In this respect it should be appreciated that staple 5 can be manufactured out of a single piece of shape memory material (i.e., so as to create an integral, monolithic structure), and the different regions of the staple worked differently, in a metallurgical sense, so that different regions of the staple have different mechanical properties and exhibit different mechanical characteristics, even as they form a single, integral, monolithic structure.

In an embodiment, the staple 5 can be manufactured so that bridge 10 is elastic, the legs 15 are elastic, and the curved hinge regions 20 are elastic, in which case the bridge 10 and the legs 15 can both be elastically deformed for providing compression to the fracture site after implantation. The bridge 10 and the legs 15 may be worked metallurgically so that they have the same or different mechanical properties.

However, in yet another embodiment, the staple 5 can be manufactured so that the bridge 10 is malleable and non-superelastic (e.g., fully annealed Nitinol, or martensitic Nitinol with an austenite start temperature greater than body temperature), and legs 15 and hinge regions 20 are superelastic (e.g., austenite but capable of forming stress-induced martensite). This allows the malleable bridge 10 of staple 5 to be inelastically bent (i.e., to take a set) to accommodate a particular geometry of the cortical anatomy, while still allowing the superelastic legs 15 of the staple to generate compression. By way of a non-limiting example, many bones exhibit an hour-glass surface profile; moreover, certain orthopedic indications (e.g., an Akin Osteotomy) often results in a cortical surface that is concave when the bones are re-approximated. In these situations, a staple with a straight bridge will not sit flush on the bone surface, which can lead to patient discomfort. In this respect it should also be appreciated that where bridge 10 is malleable and legs 15 are superelastic, legs 15 of the staple 5 may be manufactured at a more acute angle (see FIGS. 9-10) to allow for adequate fracture compression and reduction in the event that bridge 10 must be bent downward (e.g., deformed to a concave position) to meet the anatomical structure of the cortical bone.

Figure 9:
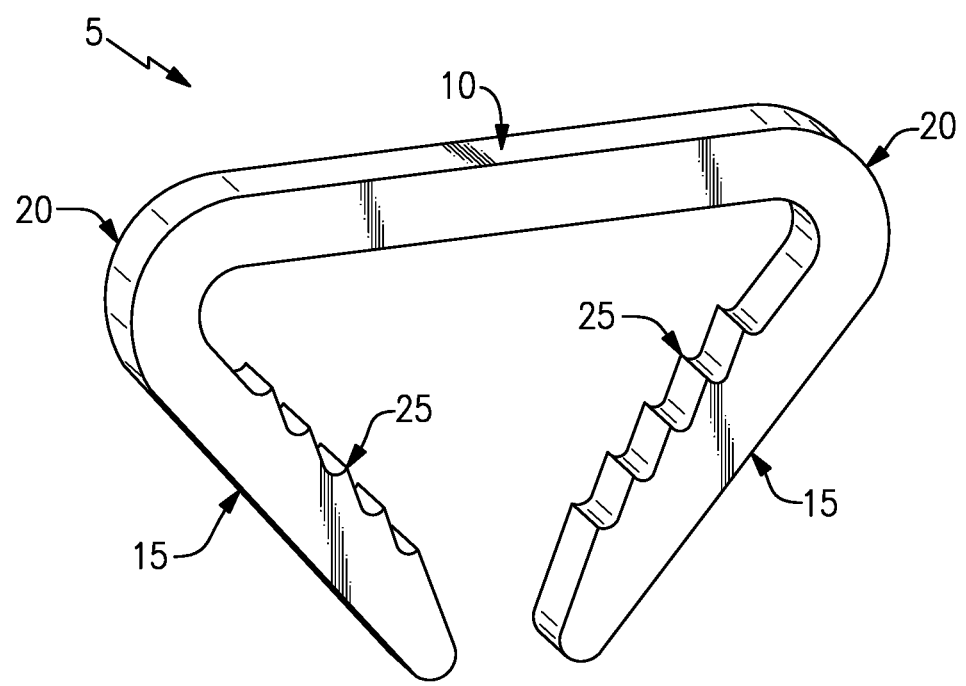
FIGS. 9 and 10 are schematic views of another novel staple formed in accordance with the present disclosure. The staple includes a malleable bridge capable of being inelastically deformed and legs which are capable of being elastically strained.
Figure 10:
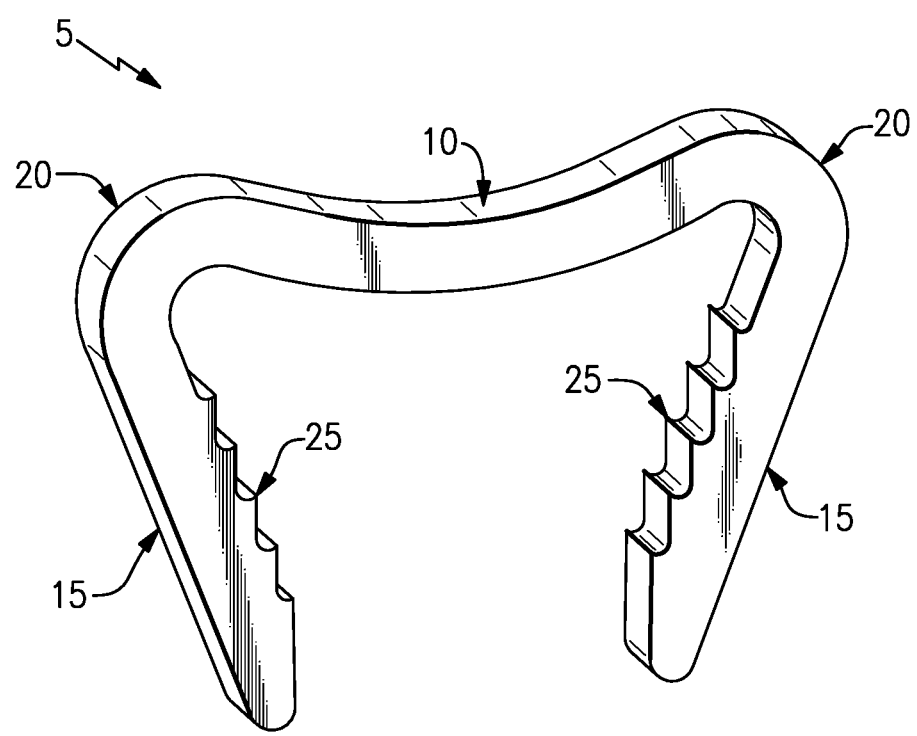

FIG. 9, for example, shows a monolithic staple 5 where bridge 10 is malleable and legs 15 are superelastic, and where staple 5 is shown in its unbent and unstrained condition, and FIG. 10 shows staple 5 where bridge 10 has been bent to give it an altered configuration. The staple 5 of FIGS. 9 and 10 may be formed out of a single piece of shape memory material, whereby to form a single, integral, monolithic structure, with the single piece of shape memory material having different regions of the staple worked differently, in a metallurgical sense, so that different regions of the staple 5 have different mechanical properties and exhibit different mechanical characteristics, i.e., bridge 10 is malleable and legs 15 are superelastic.

Figure 10A:
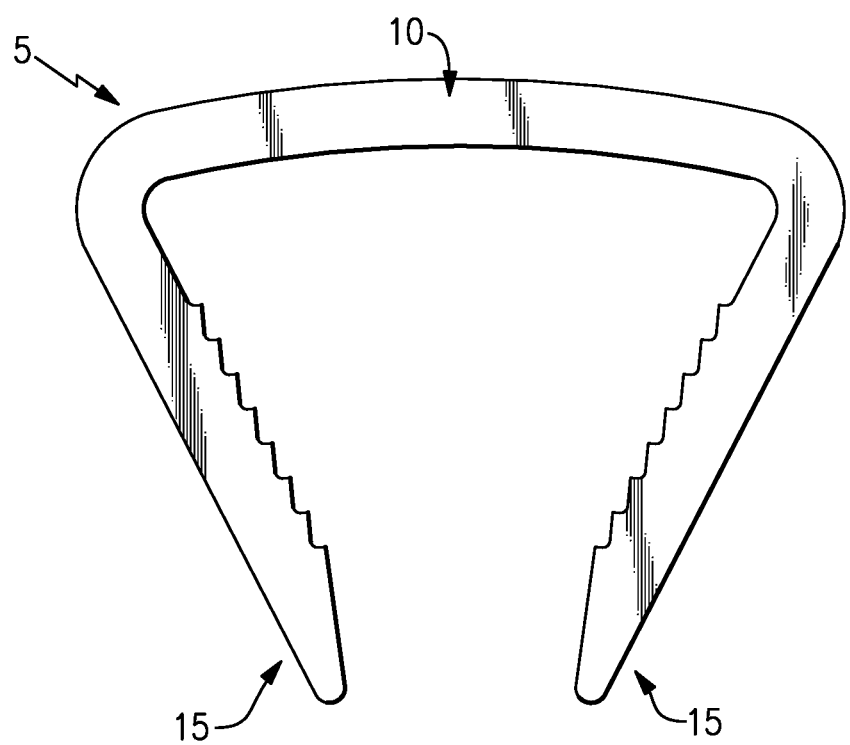
FIG. 10A is a schematic view of another novel staple formed in accordance with the present disclosure. The staple has a bridge that is convex.

It may be desirable for the staple 5 to start with a bridge that is convex, e.g., such as the staple 5 shown in FIG. 10A. This allows the bridge 10 of the implanted staple 5 to sit flush with the cortical bone surface if the bone surface is largely planar. More particularly, if the bridge 10 of staple 5 were to be linear, and the legs 15 strained and the staple 5 inserted into a prepared fracture site where the cortical surface is largely planar, the resulting implanted staple 5 could have two small "humps" at the outer ends of the bridge, i.e., at the bridge-hinge interface. Starting with a convex-shaped bridge (i.e., such as is shown in FIG. 10A) largely eliminates these "humps."

Thus, in another embodiment, the staple 5 is formed out of a single piece of shape memory material (i.e., so as to form a single, integral, monolithic structure), with the shape memory material being worked so that bridge 10 is malleable (e.g., fully annealed Nitinol, or martensitic Nitinol with an austenite start temperature greater than body temperature) and legs 15 are superelastic (e.g., austenite but capable of forming stress-induced martensite), such that bridge 10 of staple 5 may be bent to contour to the surface of the bone while the compressive force generated by the superelastic legs 15 of the staple are used to help fuse the bone.

Figure 11:
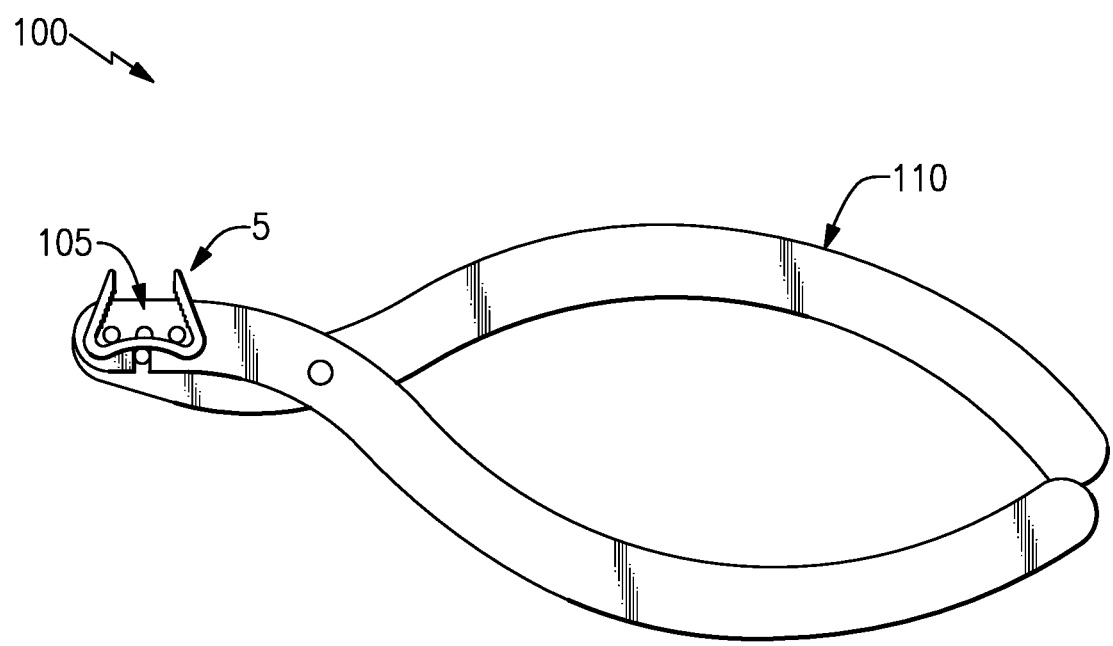
FIGS. 11 and 12 are schematic views showing an exemplary bending device which may be used with the novel staple shown in FIGS. 9 and 10 to inelastically bend the bridge of the staple to more appropriately conform to the surface profile of the cortical bone.

A bending device can be used to bend the bridge 10 of the staple 5 prior to implantation of the staple 5. An exemplary bending device 100 is shown in FIG. 11. The bending device 100 is essentially a modified plier assembly. The staple 5 is placed into the bending fixture 105 of bending device 100, and compressing the handles 110 causes the bridge 10 of the staple 5 to be bent to better meet the shape of the cortical bone surface.

Figure 12:
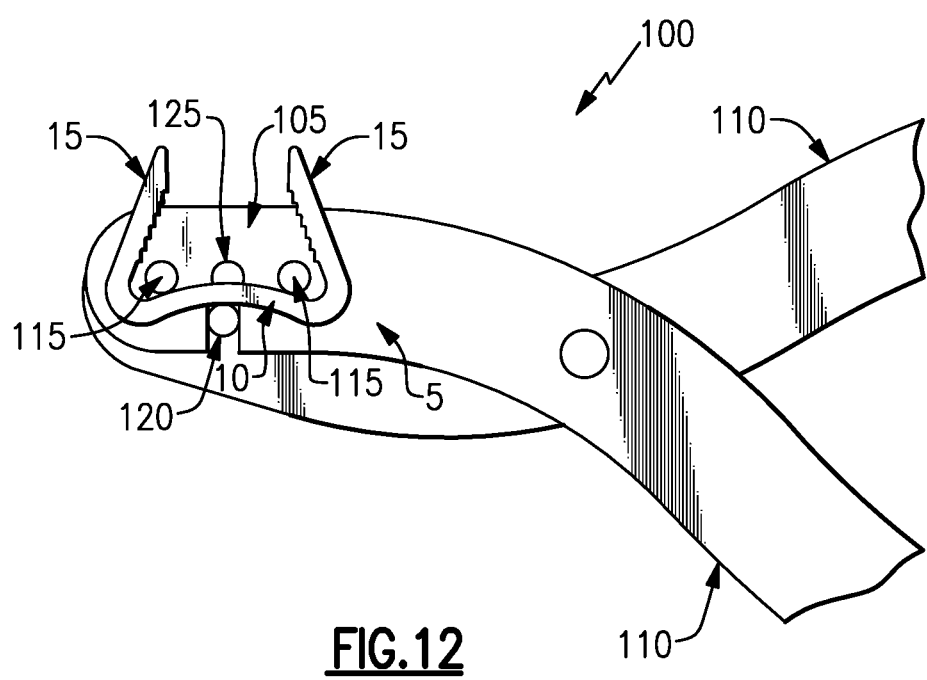

More particularly, FIG. 12 shows a close-up of the bending fixture 105 of bending device 100. Two pins 115 are used to locate the staple, and a third pin 120 is used to bend the bridge 10 of the staple 5 when the handles 110 of bending device 100 are compressed. A channel 125 in bending fixture 105 both directs the shape of the contour while also serving to limit the maximum bend imposed on the bridge 10 of the staple 5.

Figure 13:
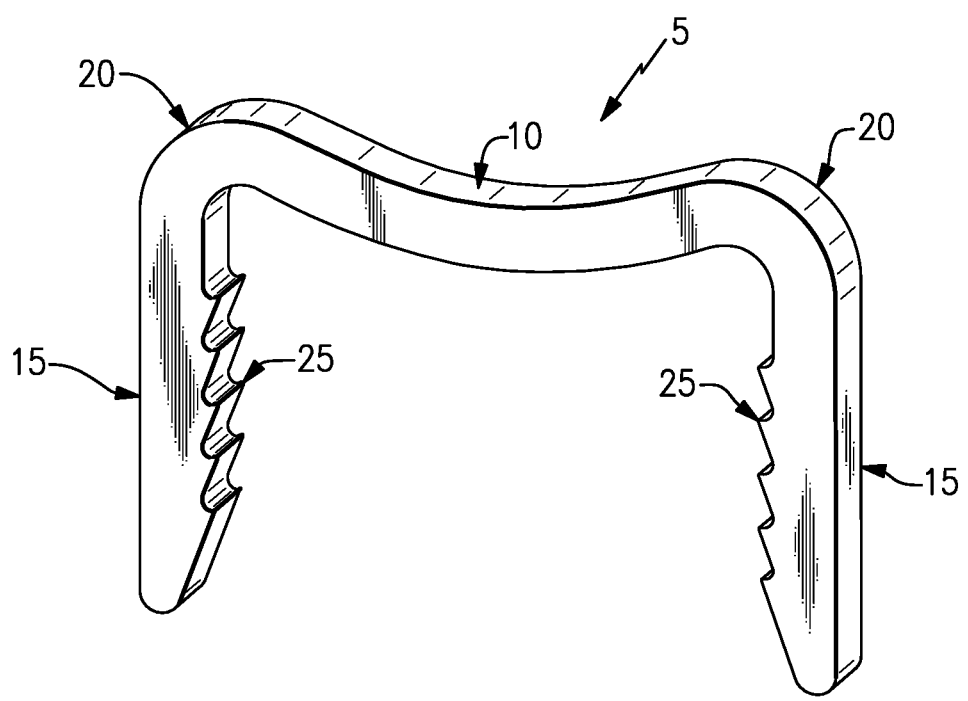
FIG. 13 is a schematic view which shows the staple of FIGS. 9 and 10 after the bridge of the staple has been inelastically bent and after the legs of the staple have been elastically strained into a parallel condition.
Figure 14:
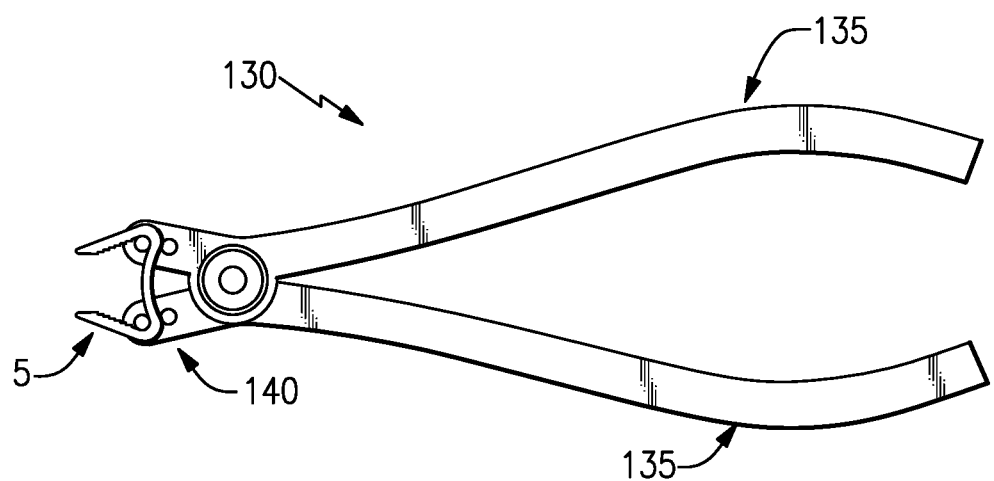
FIGS. 14, 15, and 16 are schematic views showing a plier assembly which may be used with the novel staple shown in FIGS. 9 and 10 to elastically strain (i.e., stretch) the legs of the staple after the bridge of the staple has already been inelastically bent.

After the bridge of the staple has been bent to the desired geometry (e.g., the geometry shown in FIG. 10), the legs 15 of the staple 5 can be strained open (e.g., to the geometry shown in FIG. 13) to allow the bent, strained staple 5 to be inserted into the prepared fracture site. In an embodiment, such as shown in FIG. 14, the bent staple 5 may be strained using a plier assembly 130 comprising a pair of handles 135 and a straining fixture 140. The previously-bent staple 5 is placed into the straining fixture 140, and then compressing the handles 135 causes the staple's legs 15 to be strained opened to parallel. The plier assembly 130 can also be used to insert the staple 5 into the bone after the legs 15 of the staple 5 have been strained open to substantially parallel.

Figure 15:
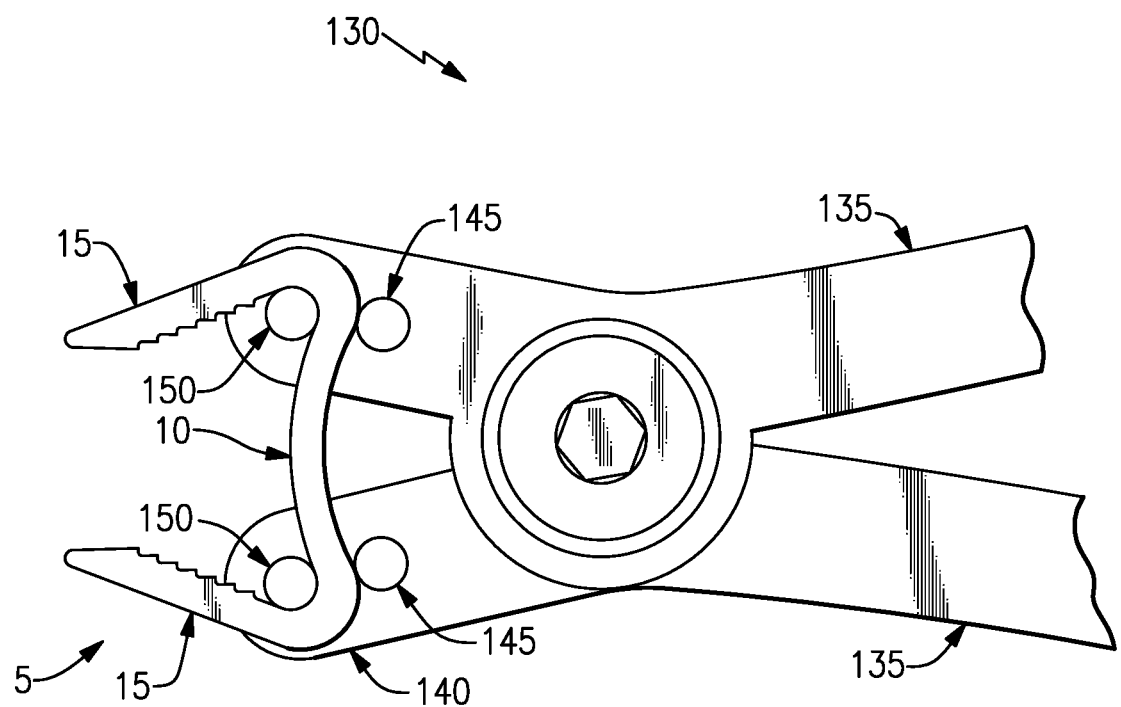
Figure 16:
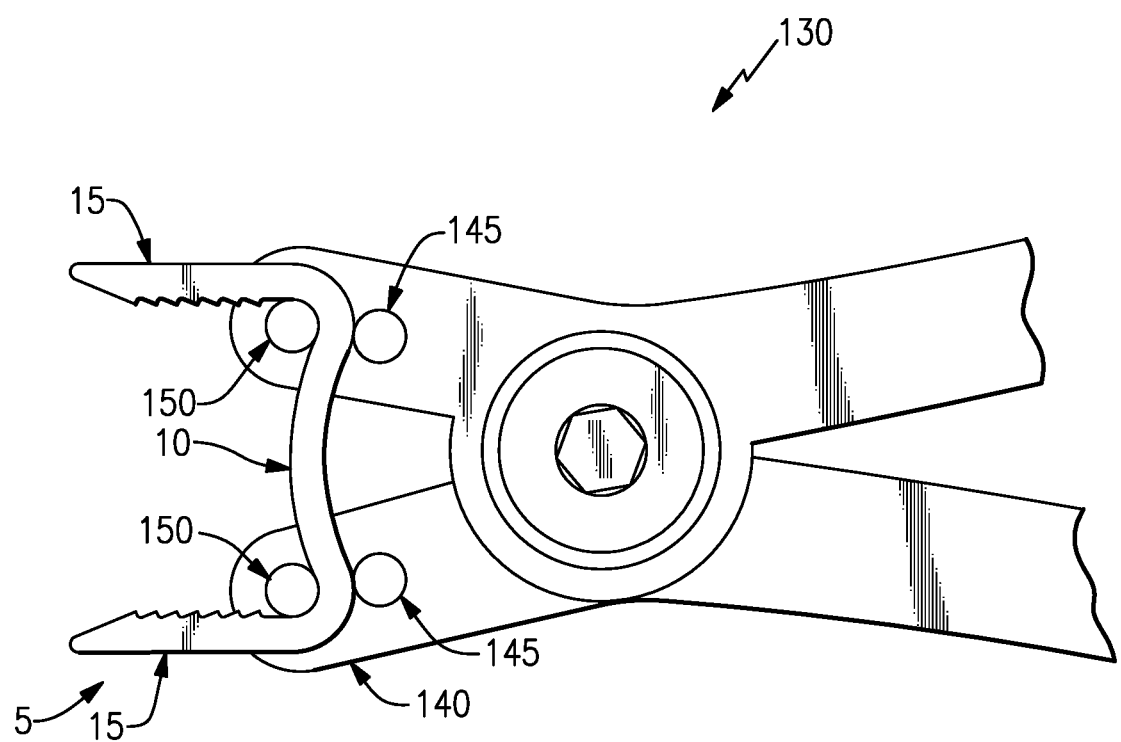

FIGS. 15 and 16 show the construction and function of the straining fixture 140 of the plier assembly 130 in greater detail. The staple 5 is supported by two internal pins 145 and two external pins 150. Compressing the handles 135 causes the staple legs 15 to move from an inward-pointing or converging configuration (see FIG. 15) to a more open (e.g., parallel) state (see FIG. 16). The previously-bent staple 5, with the legs 15 now strained to the open state, is then ready for implantation across the fracture line. When implanted in bone and thereafter released from the plier assembly 130, the strained legs 15 of staple 5 then kick inward, reducing the fracture and generating and maintaining compression across the fracture.

Figure 17:
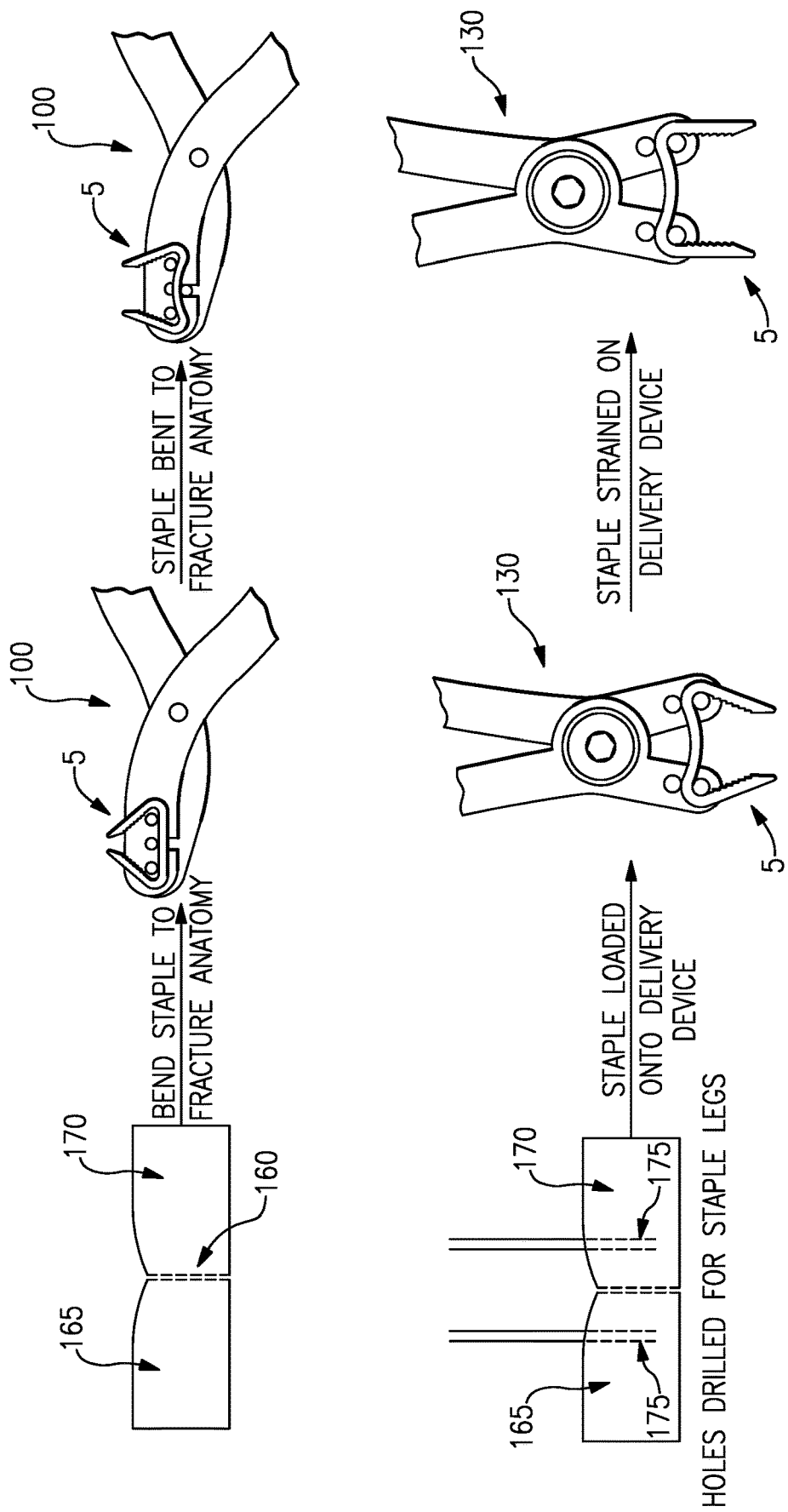
FIGS. 17 and 18 are schematic views showing how the novel staple shown in FIGS. 9 and 10 may have the bridge of the staple inelastically bent to conform to the surface profile of a bone. The legs of the staple are elastically bent into a parallel condition, and the staple is thereafter deployed in bone so as to provide compression across a fracture.
Figure 18:
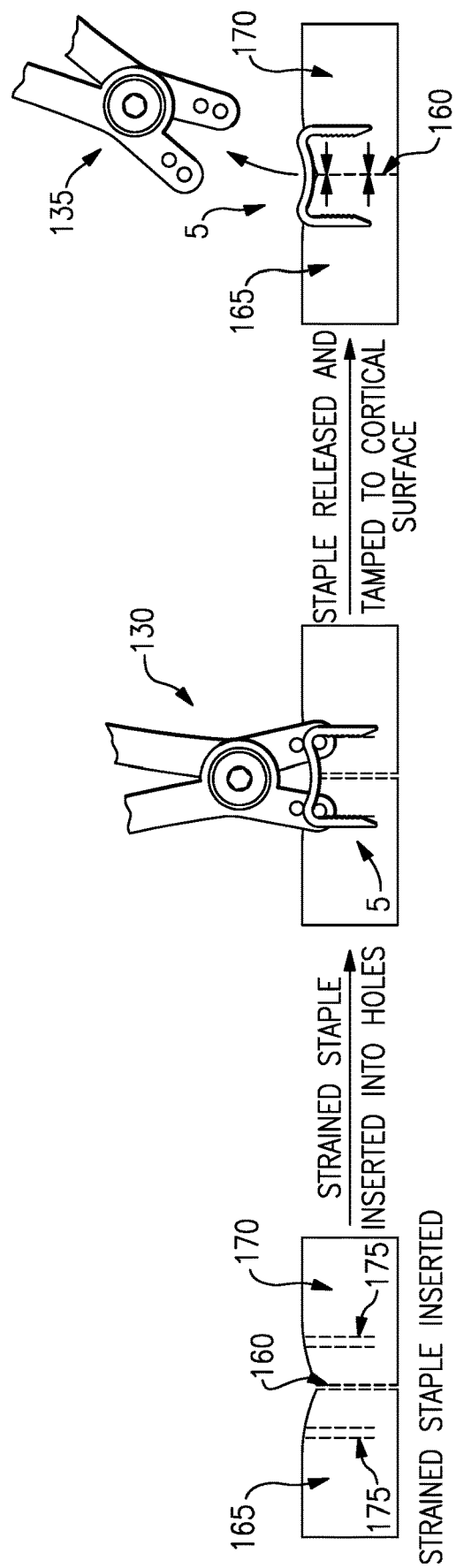

FIGS. 17 and 18 illustrate how a staple 5 formed out of a shape memory material, with its bridge 10 being malleable (e.g., fully annealed Nitinol, or martensitic Nitinol with an austenite start temperature greater than body temperature) and its legs 15 being superelastic (e.g., austenite but capable of forming stress-induced martensite), may be used to reduce a fracture 160 between two bone fragments 165, 170 and generate and maintain compression across the fracture 160. Significantly, because the bridge 10 of the staple 5 is malleable and the legs 15 of the staple 10 are superelastic, the bridge 10 of the staple 5 can be first bent to match the surface profile of the bone while enabling the superelastic legs of the staple to be elastically strained to provide the compressive force across the fracture 160.

In an embodiment, the staple 5 is first loaded onto the bending device 100 and the bridge 10 of the staple 5 is bent to accommodate the surface profile of the patient's cortical bone anatomy. The surgeon may use fluoroscopy or trial-and-error to bend the bridge 10 of the staple 5 to the appropriate configuration. With the bridge 10 of the staple 5 appropriately bent, a drill guide (not shown) is used to drill holes 175 into the bone fragments 165, 170 at the appropriate locations on either side of the fracture 160 to accommodate the strained staple legs 15. The staple 5 is then loaded onto the plier assembly 130, and the superelastic legs 15 are then elastically bent to the open state.

With the bridge 10 of the staple 5 inelastically bent into the appropriate configuration and with the legs 15 of the staple 5 elastically strained to substantially parallel, the staple 5 can be inserted into the pre-drilled holes 175 in bone fragments 165, 170. The staple 5 is then released from the plier assembly 130 and tamped to sit flush with the cortical surface, with the inelastically bent bridge 10 of the staple 5 more closely matching the surface contour of the bone. The elastically-strained superelastic legs 15 of the staple 5 apply a compressive force across the fracture 160.

If desired, in embodiments where the staple 5 is provided with a malleable bridge 10, the malleable bridge 10 may be bent, or further bent, after the staple 5 has been deployed in bone, e.g., to match, or to more closely match, the surface profile of the bone.

Figure 19:
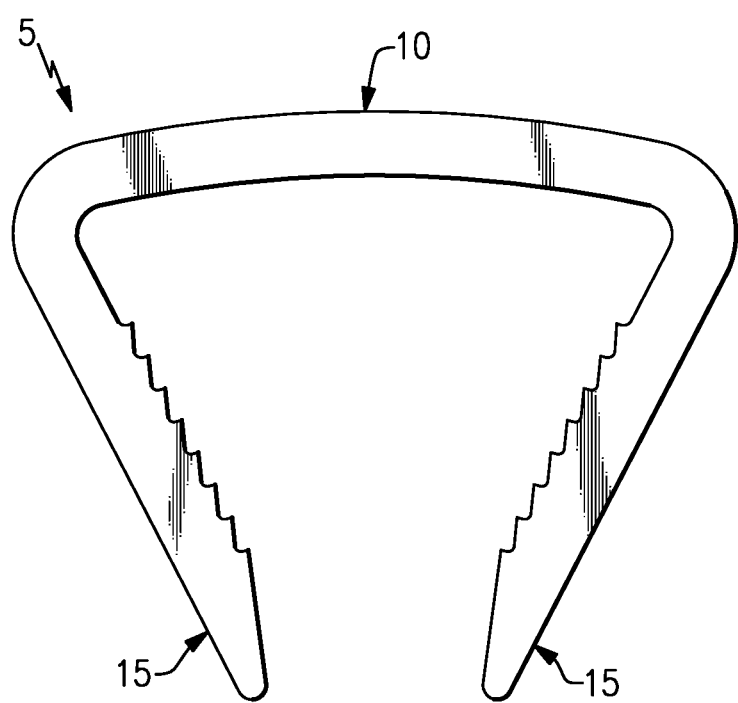
FIG. 19 is a schematic view of another novel staple formed in accordance with the present disclosure. The staple includes a malleable bridge capable of being inelastically deformed and legs which are capable of being elastically strained. The bridge of the staple has been deformed to have a convex configuration after bending.

In other embodiments, the bone may have a convex profile. In such an embodiment, it may be desirable to set the staple 5 so that its bridge 10 has a convex configuration. To this end, and looking now at FIG. 19, there is shown a staple 5 which has been inelastically bent to have a convex bridge 10 and two legs 15.

Figure 20:
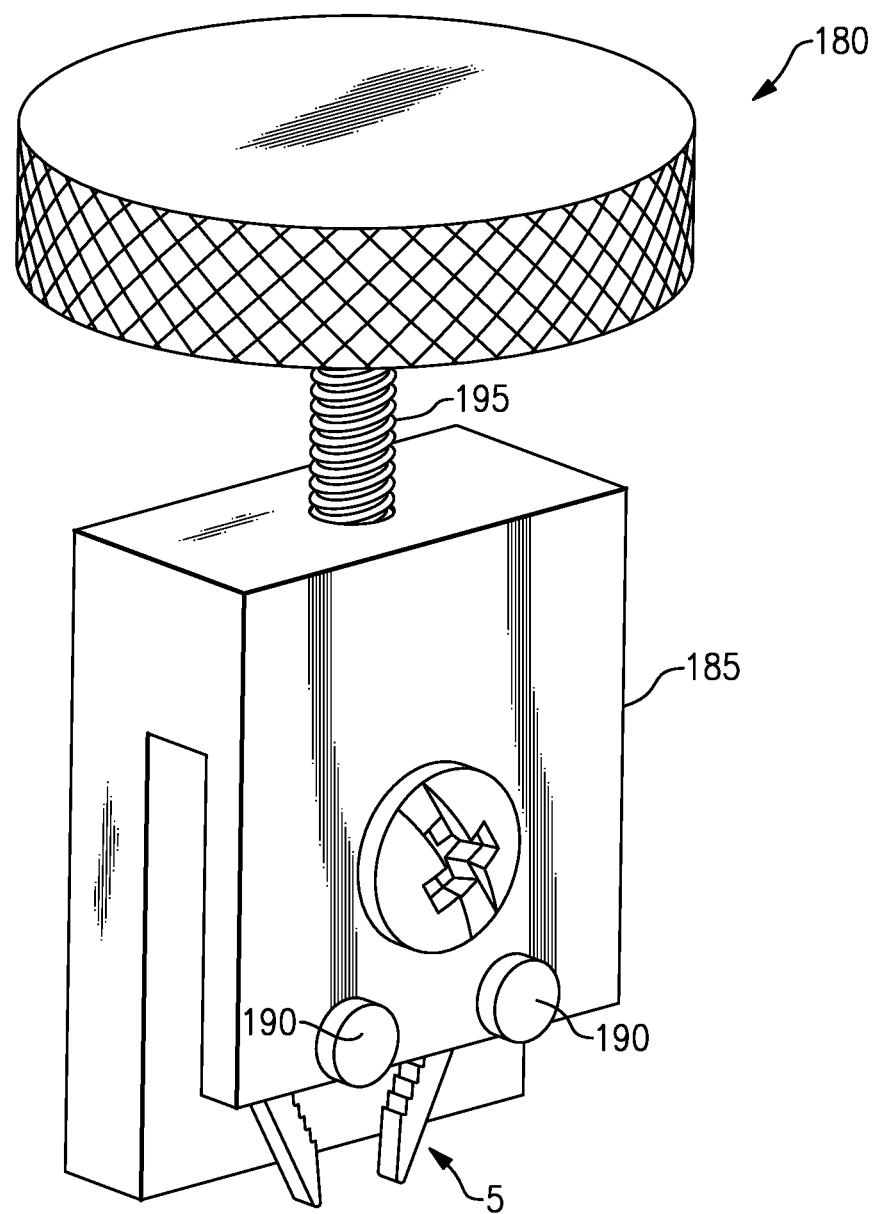
FIGS. 20 and 21 are schematic views of another novel device which may be used to bend the bridge of the staple shown in FIG. 10A.
Figure 21:
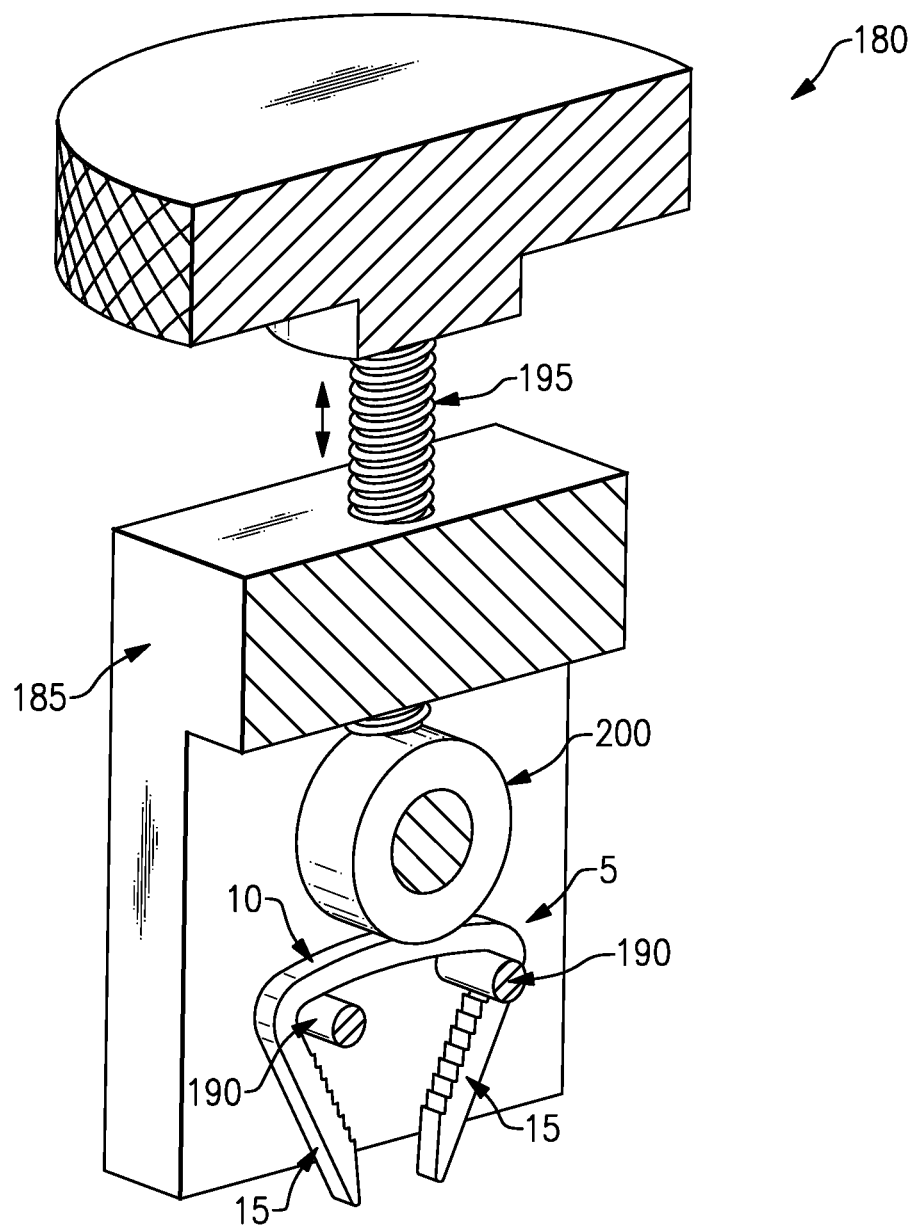
Figure 22:
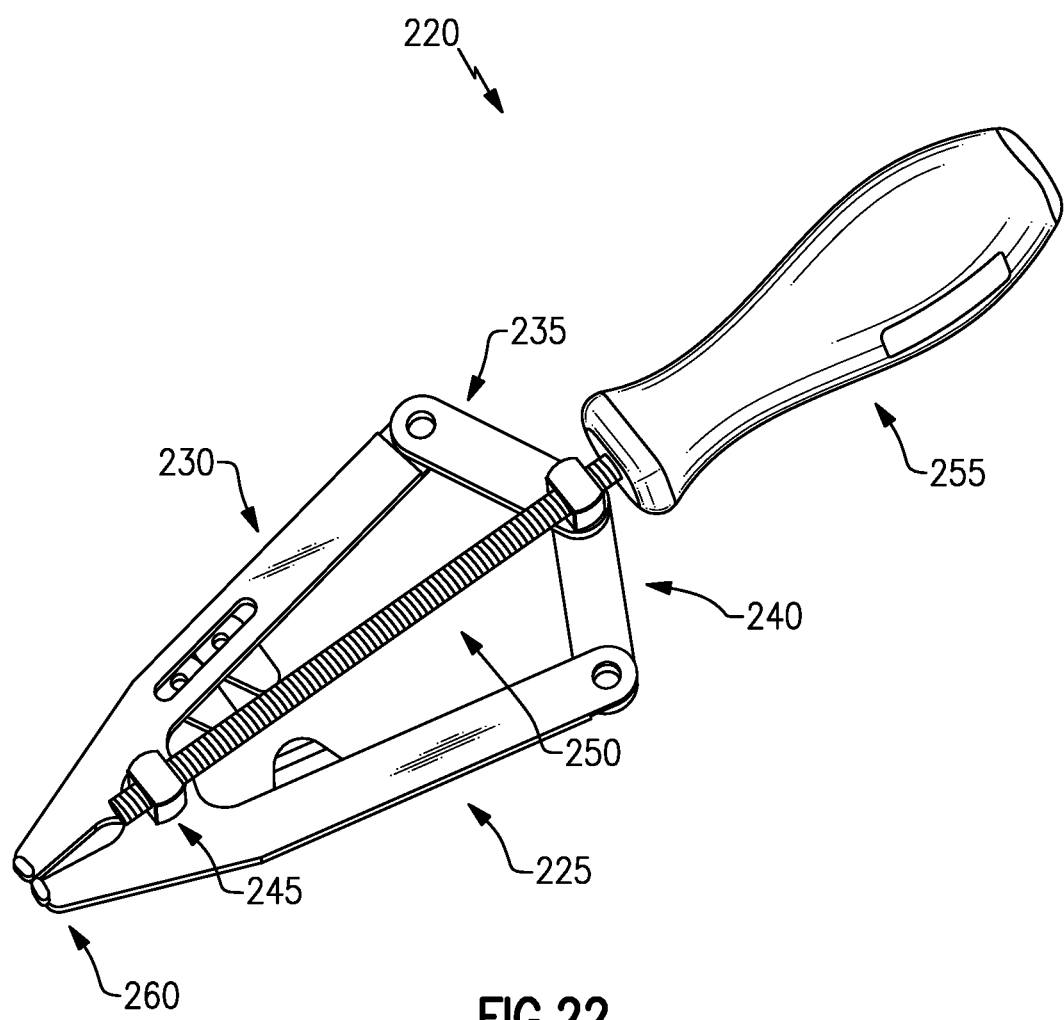

FIGS. 20 and 21 illustrate another exemplary bending device 180 which may be used to bend the bridge 10 of a staple 5, e.g., the bridge 10 of the staple 5 shown in FIG. 10A. The bending device 180 generally includes a housing 185 supporting a pair of pins 190. The pins 190 receive the staple 5 in the manner shown in FIG. 21. The bending device 180 also includes a screw mechanism 195 which selectively advances an element 200 toward pins 190 or retracts element 200 away from the pins 190. As a result of this construction, when the staple 5 is mounted on the pins 190, the screw mechanism 195 can be used to drive element 200 against the bridge 10 of the staple 5 to bend the bridge 10.

If desired, the staple 5 could be used to attach soft tissue to bone (e.g., to attach a rotator cuff to bone). It should be appreciated that the delivery device 130 discussed above may not always seat the staple 5 with the bridge 10 of the staple 5 seated directly against the cortical surface of the bone (i.e., the bridge of the staple may sit slightly above the cortical surface of the bone). Therefore, a tamp of the sort well known in the art may be used to fully seat the staple bridge 10 against the cortical surface of the bone.

In another embodiment, the staple 5, the bending device 100 and/or the bending device 180, and the delivery device (i.e., plier assembly) 130 are provided as a system in the form of a sterilized kit. The kit may include additional instruments to aid in the implantation of the staple (e.g., k-wire, drill bit, staple size guide, tamp, etc.).

FIGS. 22-28 illustrate a combination bending device and delivery device 220. Combination device 220 has plier legs 225, 230 which connect to links 235. Plier legs 225, 230 and links 235 are connected with threaded bosses 240 and 245. Threaded bosses 240 and 245 are coupled by a threaded rod 250. The threaded rod 250 has a handle 255. Turning the handle 255 clockwise causes the plier legs 225, 230 to become more parallel to each other (see, e.g., FIG. 24).

Figure 23:
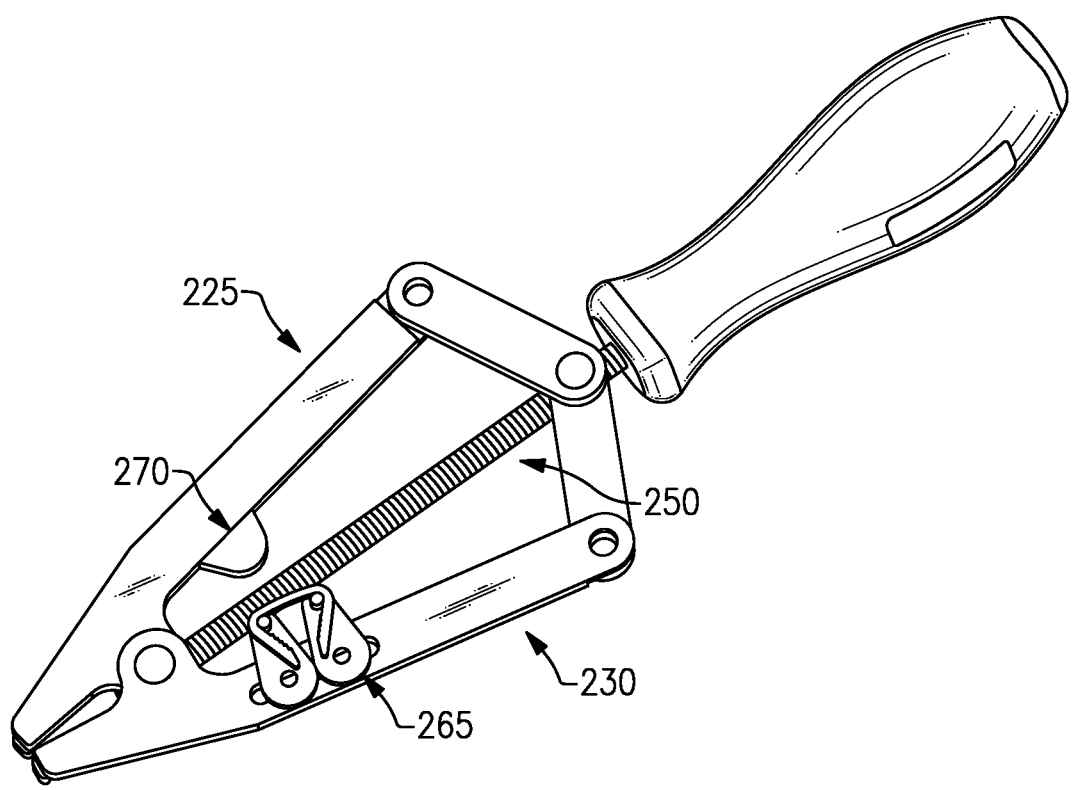
Figure 25:
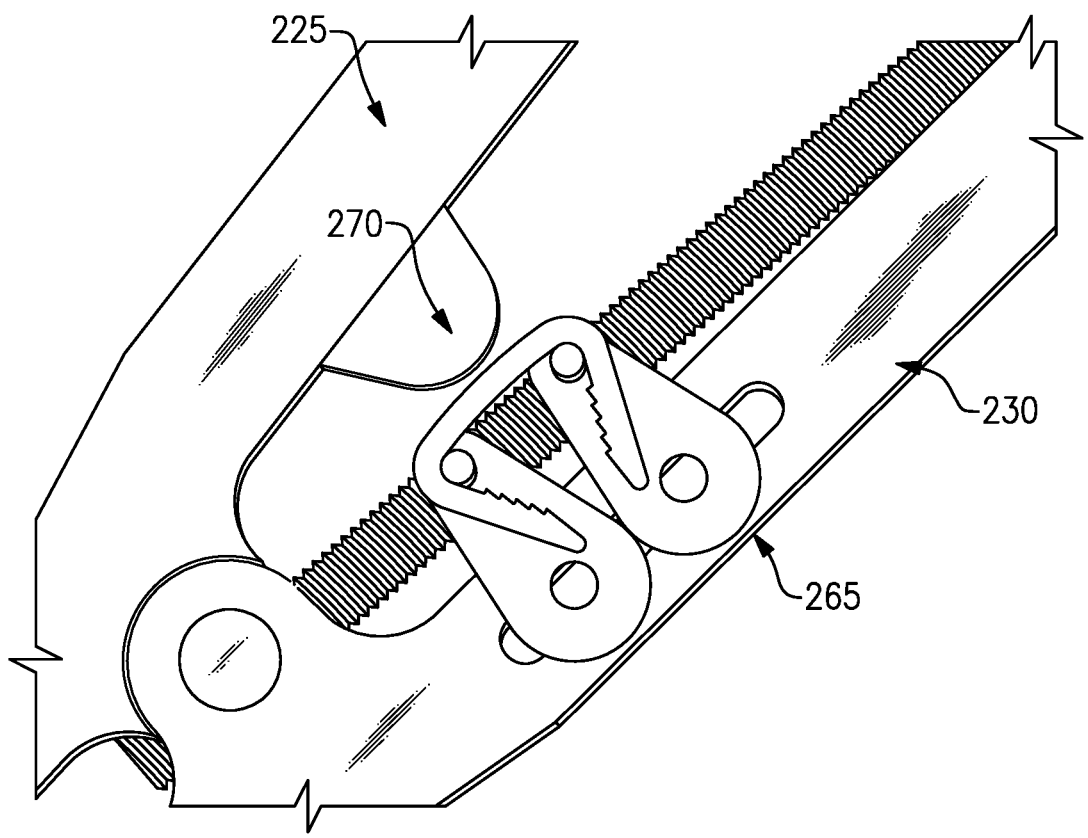
Figure 26:
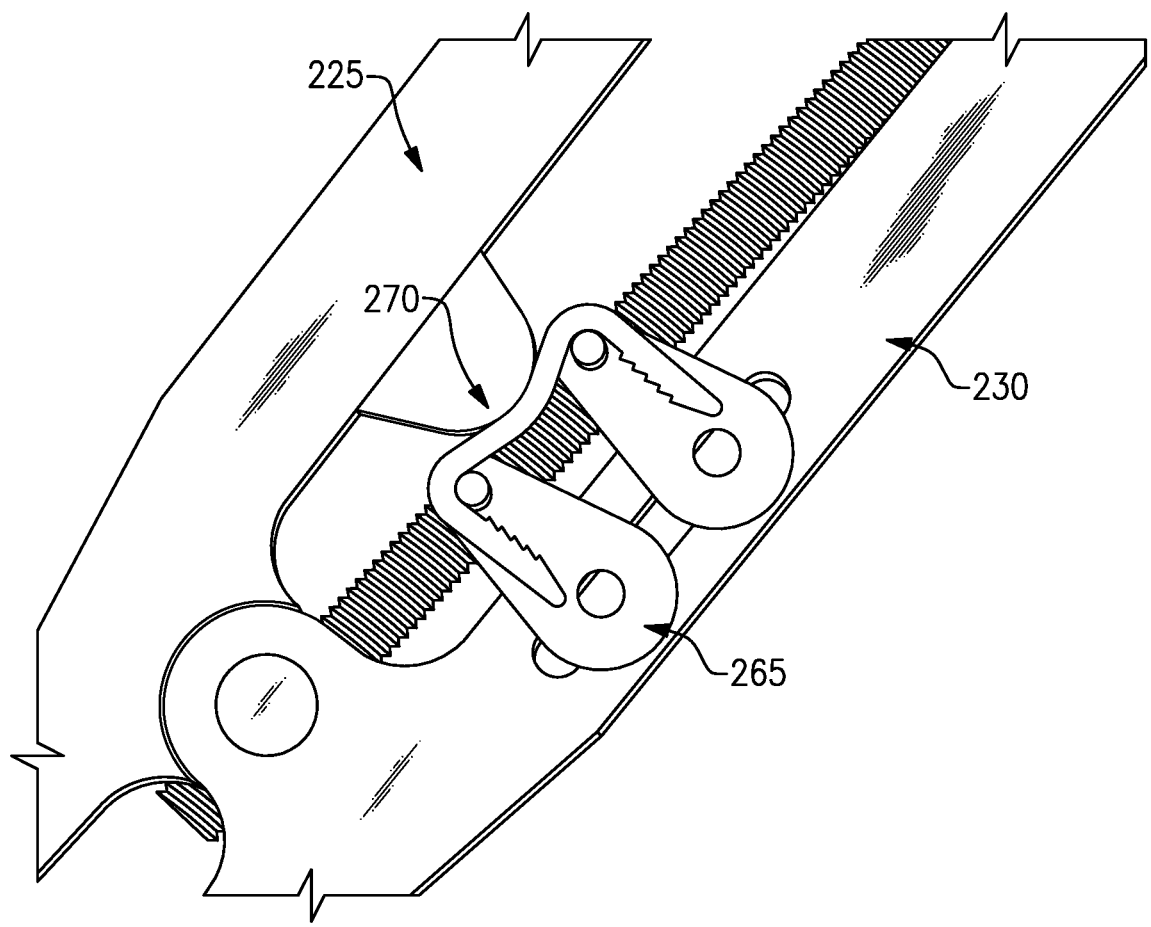
Figure 27:
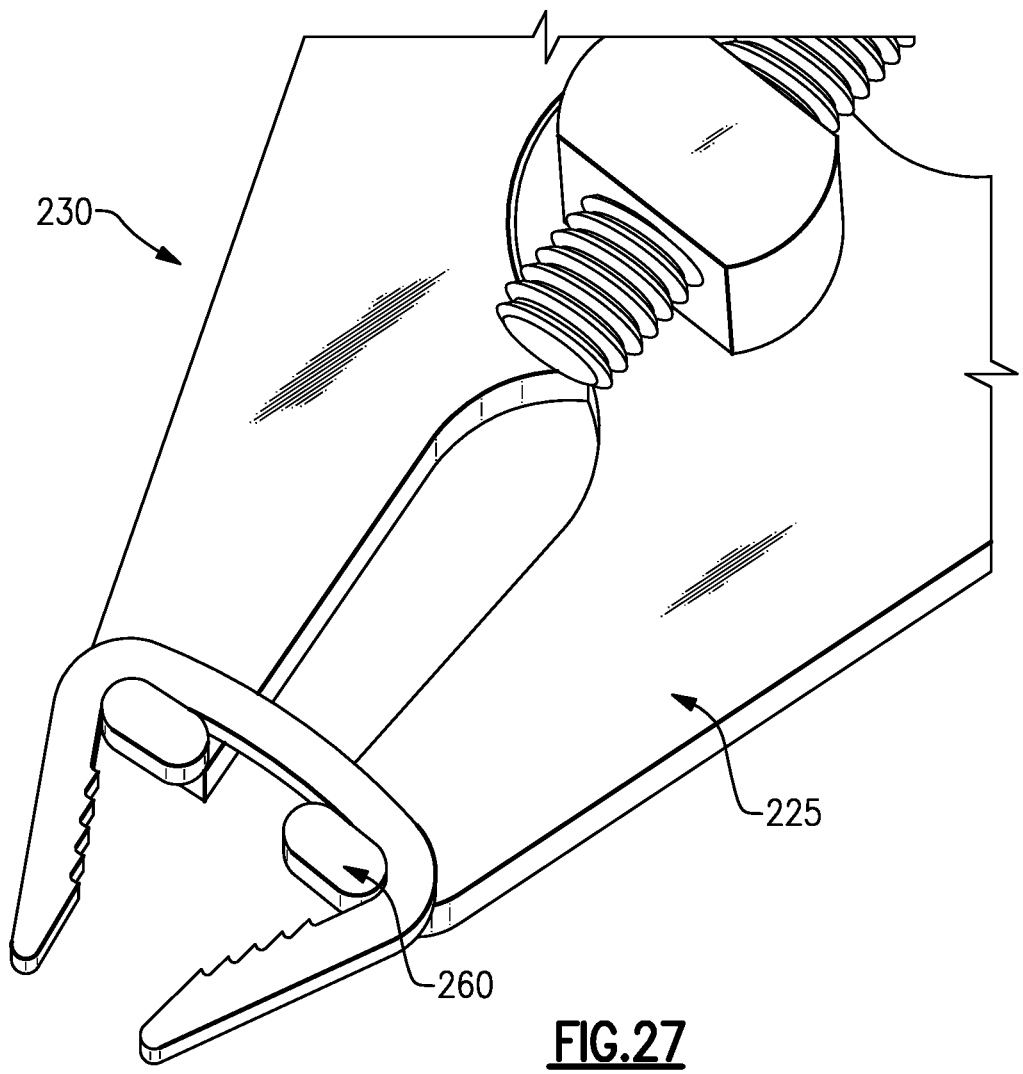
Figure 28:
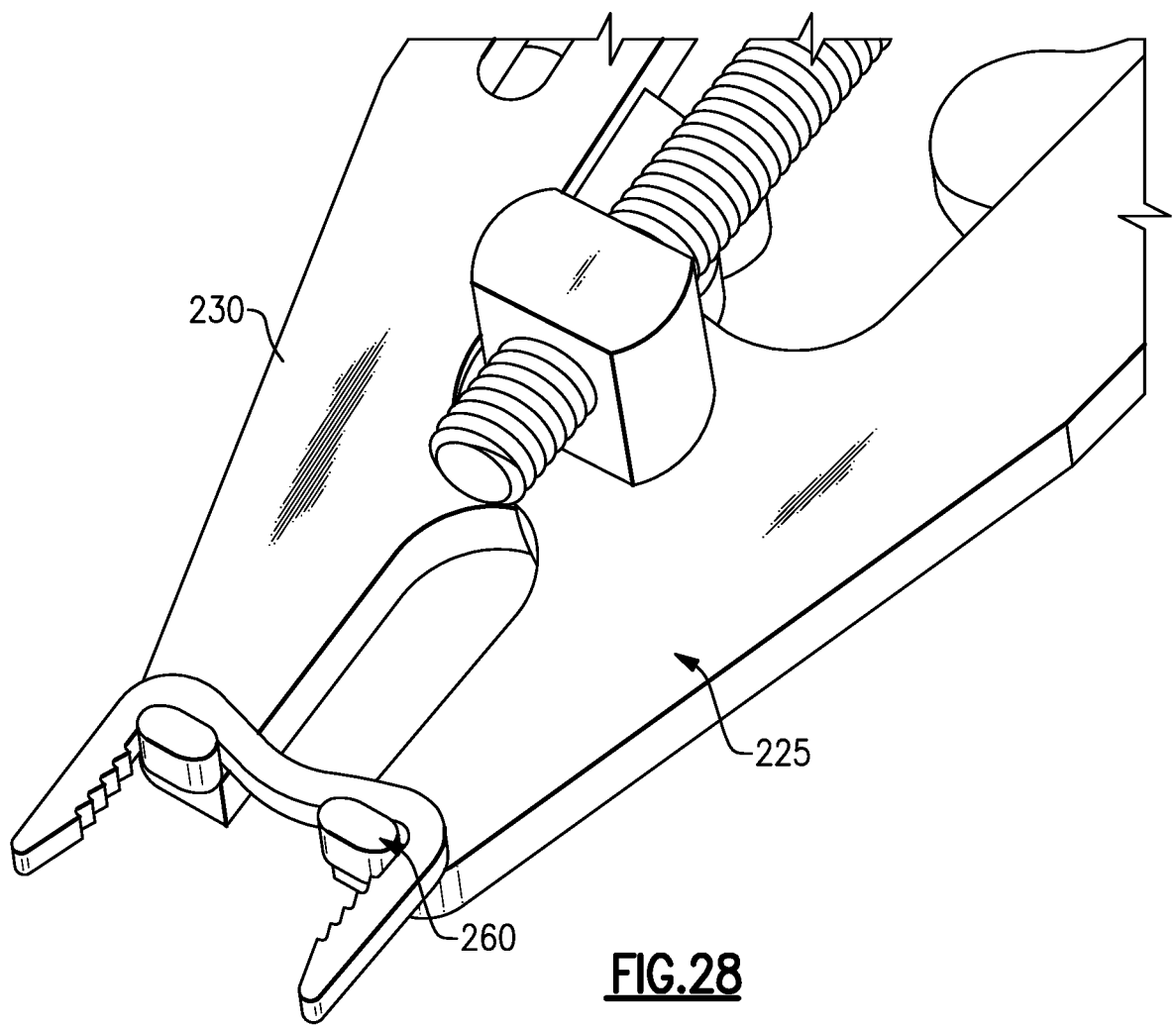
Figure 29:
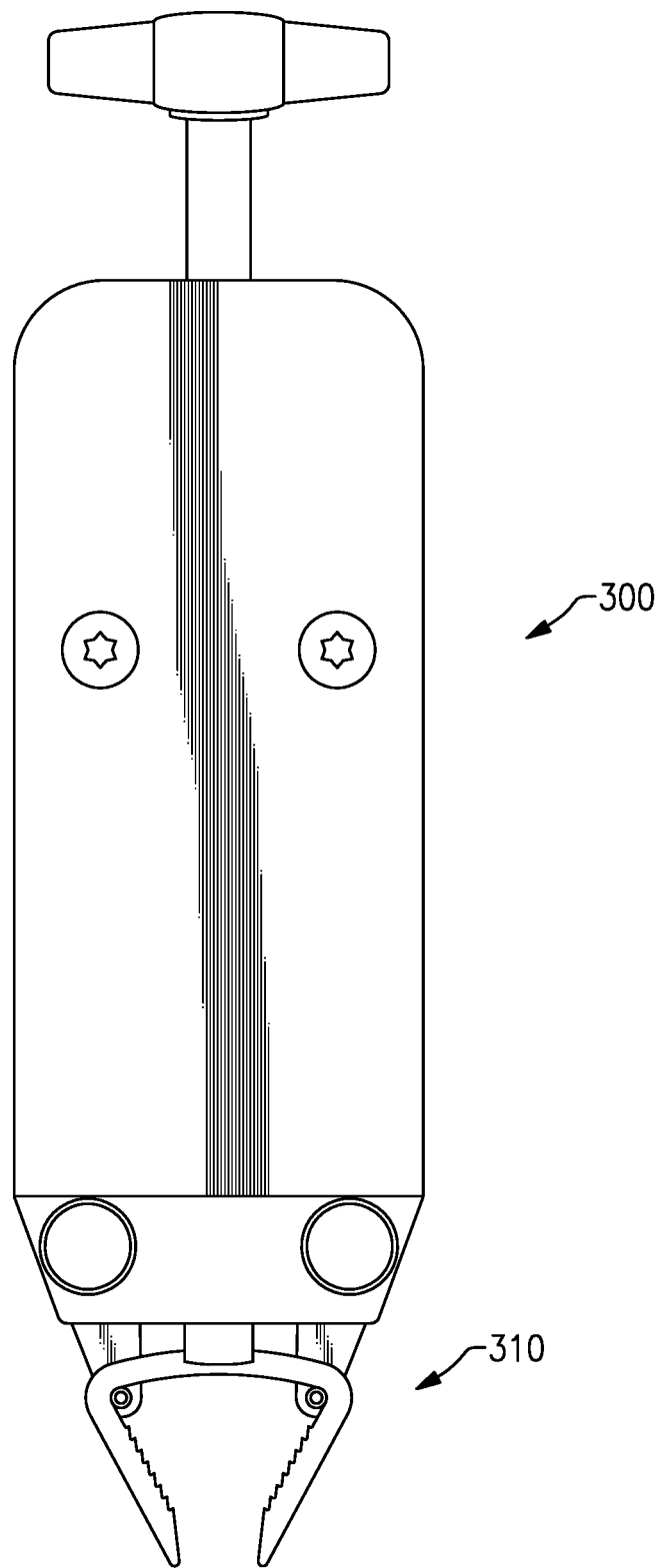
FIG. 29 illustrates an exemplary surgical system. The surgical system includes a delivery device and a staple.
Figure 30:
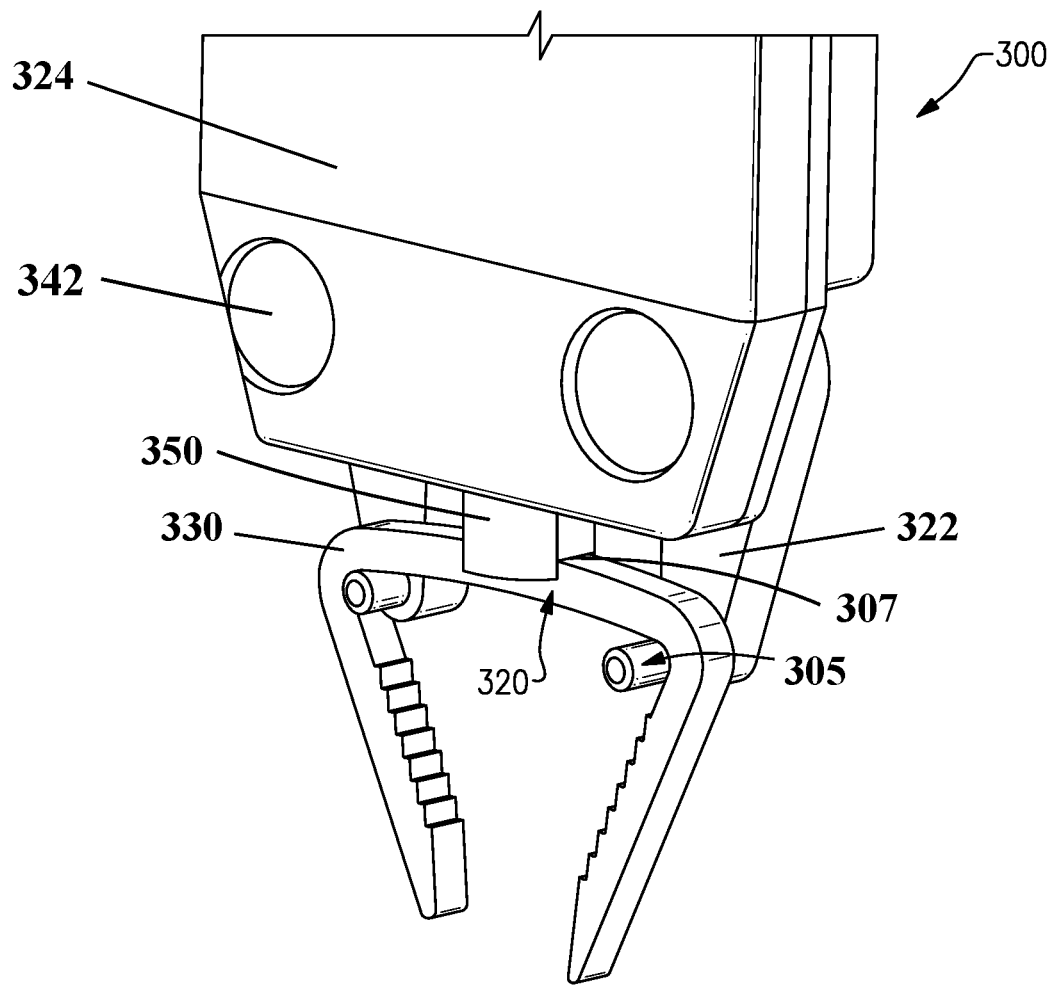
FIG. 30 schematically illustrates the delivery device of the surgical system of FIG. 29 engaging the staple.

Referring to FIG. 23, the back side of the combination bending device and delivery device 220 is shown. A staple holder 265 is attached to plier leg 230 and a bending anvil 270 extends from the plier leg 225. When the staple 5 is placed onto the staple holder 265 and the anvil 270 is pressed against the staple 5 by turning the screw 250 clockwise, the anvil 270 bends the bridge 10 of the staple 5 (see, e.g., FIGS. 25 and 26).

After the staple 5 has had the bridge 10 bent, the staple 5 can be prepared for implantation. The ends of the plier legs 225 and 230 have staple grips 260 which engage the hinge region of the staple 5 (see, e.g., FIGS. 27-28). When the plier legs 225 and 230 are moved to a parallel position, the legs 15 of the staple 5 become more parallel. With the staple 5 mounted to the legs 225, 230 of the combination bending device and delivery device 220, the combination device 220 is used to insert the staple 5. The surgeon can gradually release the staple 5 from the combination device 220 by articulating the legs 225, 230 away from the parallel position.

Conventional shape memory staples typically generate between about 20 N and about 120 N of compressive force from the staple legs kicking inward. The staples of the present disclosure which include a stretched bridge generate a compressive load of greater than the 20 N to 120 N generated by other like-sized conventional staples, thereby providing significantly increased compressive forces without tearing through or otherwise damaging the bone. Additionally, the compressive force provided by the stretched bridge staples of the present disclosure are more uniformly distributed across the fracture line (i.e., across the cortical bone and the cancellous bone).

An additional exemplary surgical system is illustrated with respect to FIGS. 29-35. The surgical system includes a delivery device 300 and a staple 310. The delivery device 300 can be used for implanting staples 310 that do not have holes in their hinge regions. Such a staple 310 is shown attached to the delivery device 300 in FIG. 29. A first leg 360 of the staple 310 is connected to a bridge 320 by a first hinge region 330, and a second leg 370 of the staple 310 is connected to the bridge 320 by a second hinge region 330. In an embodiment, and referring to both FIGS. 29 and 30, the delivery device 300 may engage the staple 310 on an inner surface of the first hinge region 330 and an inner surface of the second hinge region 330 that are both underneath the staple bridge 320. More specifically, the delivery device 300 may engage the staple 310 underneath the hinge regions 330. The delivery device 300 also includes pins 305 that may engage the staple 310 underneath the staple bridge 320 and more specifically underneath the hinge region 330. As shown in FIGS. 29 to 35, the pins 305 engage the bridge 320 of the staple 310 on a common side of the bridge 320. The delivery device 300 includes arms 322 attached to a body 324, and a pin 305 is connected to each arm 322. In one example, the pins 305 extend from the arms 322 in the same direction. In one example, the body 324 defines a plane that passes through the legs 360 and 370 and the bridge 320 of the staple 310, and the arms 322 are located on a common side of the plane. The two arms 322 are pivotally connected to the body 324 at a pivot point 342 (shown in FIGS. 30 and 32) with a pivot pin (not shown).

Figure 31:
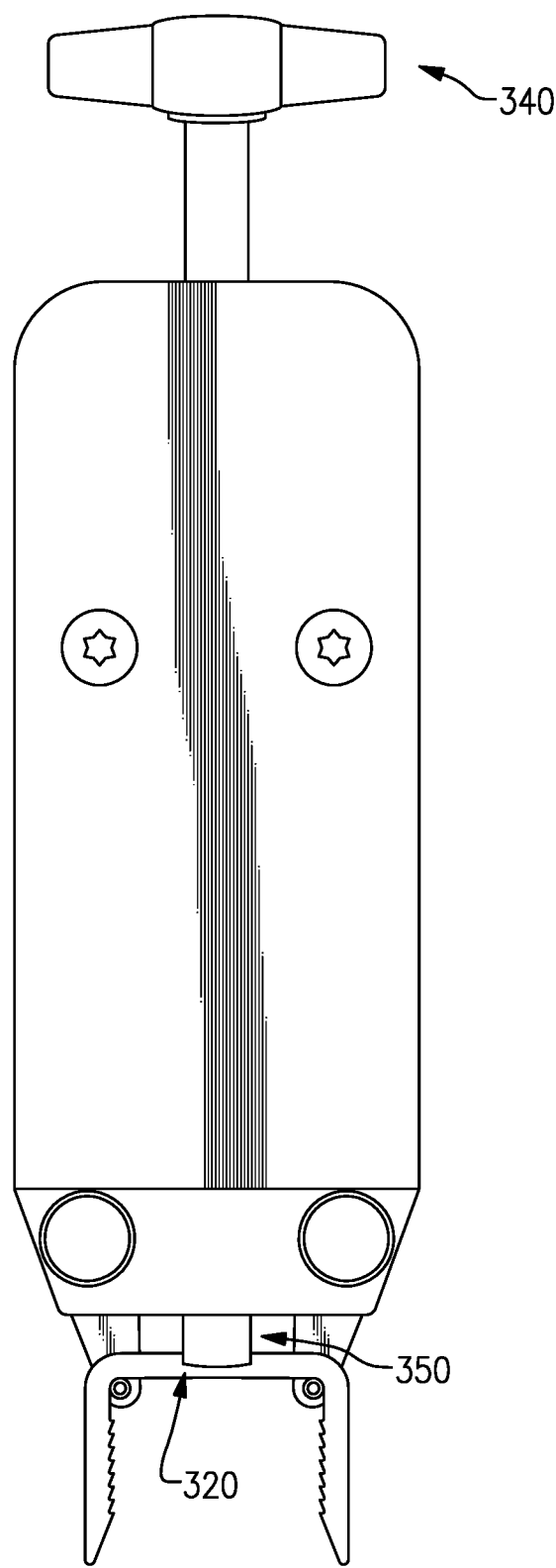
FIGS. 31 and 32 schematically illustrate the use of the delivery device of the surgical system of FIG. 29 to move the staple to a deformed state.
Figure 32:
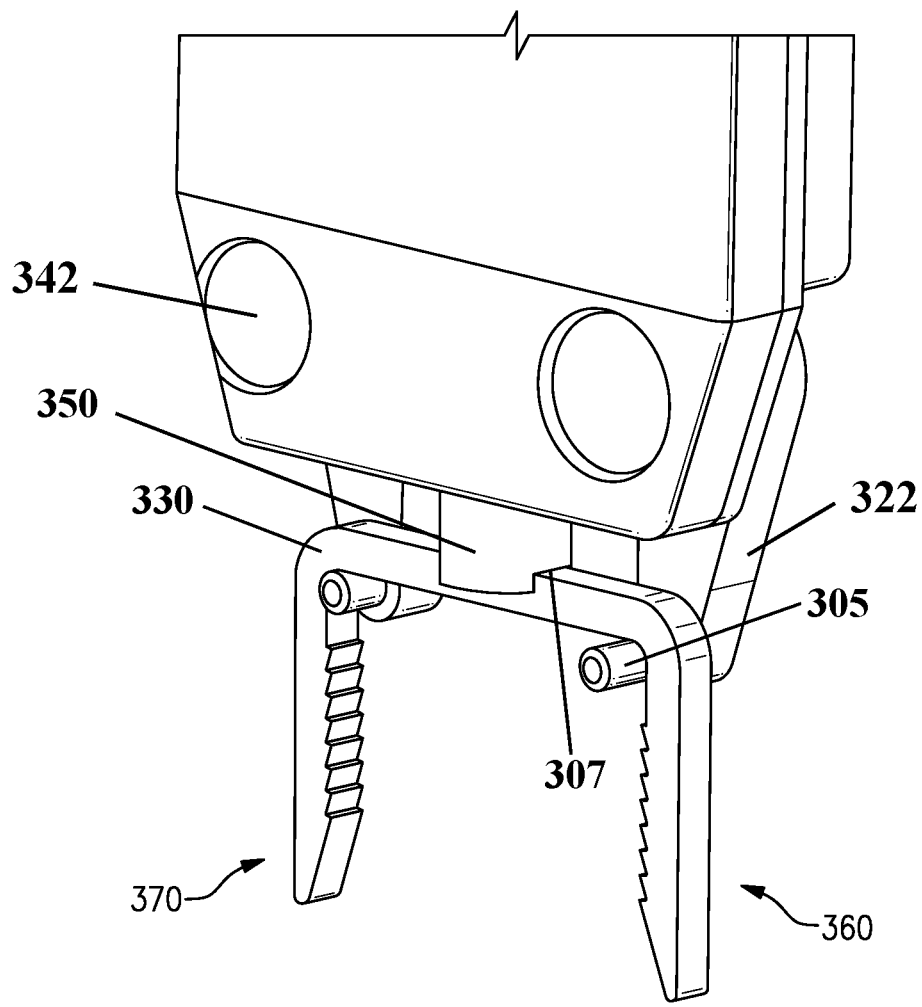

Referring to FIG. 31, rotating a knob 340 of the delivery device 300 causes a plunger 350 to move along a plunger longitudinal axis X in a direction to deform the staple bridge 320. The plunger 350 is attached to a knob 342 at a proximal end of the delivery device 300 and a proximal end of the plunger 350. In the deformed state, as is shown in FIG. 32, the staple legs 360 and 370 are parallel to each other for insertion into prepared bone holes. Turning the knob 340 counterclockwise moves the plunger 350 along the plunger longitudinal axis X and in an opposite direction and releases the strain on the staple bridge 320 and allows the staple 310 to re-assume a convergent position. As shown in FIGS. 29 to 35, a distal end of the plunger 350 includes a notch 307, and the bridge 320 of the staple 310 is received in the notch 307 of the plunger.

An additional exemplary surgical system is illustrated with respect to FIGS. 29-35. The surgical system includes a delivery device 300 and a staple 310. The delivery device 300 can be used for implanting staples 310 that do not have holes in their hinge regions. Such a staple 310 is shown attached to the delivery device 300 in FIG. 29. In an embodiment, and referring to both FIGS. 29 and 30, the delivery device 300 may engage the staple 310 underneath a staple bridge 320 and more specifically underneath a hinge location 330.

Referring to FIG. 31, rotating a knob 340 of the delivery device 300 causes a plunger 350 to deform the staple bridge 320. In the deformed state, as is shown in FIG. 32, the staple legs 360 and 370 are parallel to each other for insertion into prepared bone holes. Turning the knob 340 counterclockwise releases the strain on the staple bridge 320 and allows the staple 310 to re-assume a convergent position.

Figure 33:
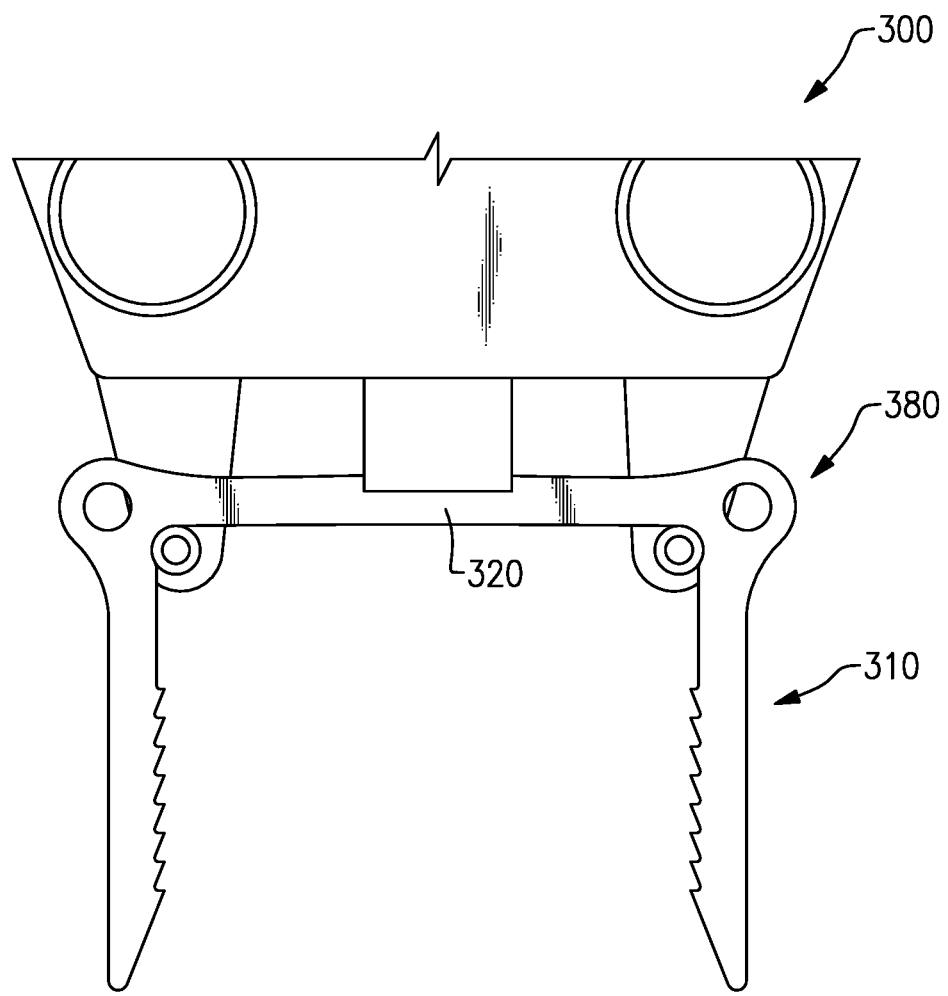
FIG. 33 illustrates another exemplary surgical system. The surgical system includes a delivery device and a staple.

Referring now to FIG. 33, the delivery device 300 may also be used to implant staples 310 that have holes 380 in the hinge region. The delivery device 300 does not have to engage the staple 310 in the holes, however. Instead, the delivery device 300 can engage the staple 310 under the bridge 320.

Figure 34:
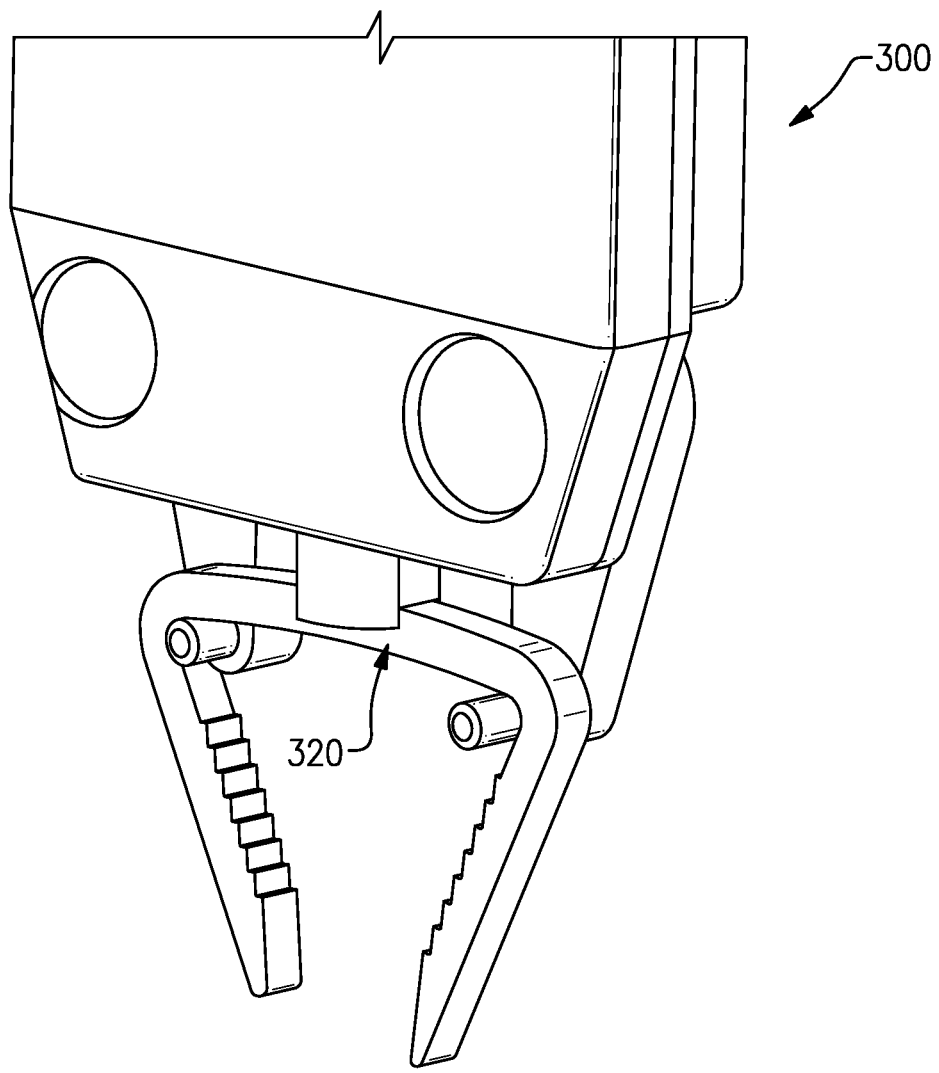

As shown in FIGS. 34-35, the delivery device 300 can be used to cause staple bridge 320 to take a permanent set. The staple bridge 320 may be first heat treated to be fully annealed and or martensitic at body temperature. Turning the knob 340 of the delivery device 300 causes the plunger 350 to permanently deform the staple bridge 320 to a concave state (see, e.g., FIG. 34). This causes staple legs 360 and 370 to become parallel. It should be appreciated that releasing the strain on staple bridge 320 after the legs 360, 370 are in the parallel position will cause staple legs 360 and 370 to assume a convergent position.

Figure 37:
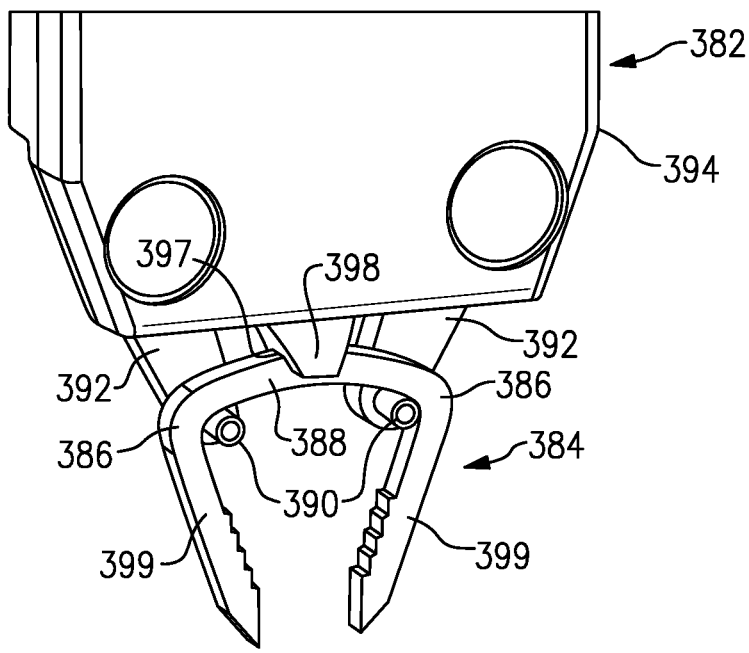

FIGS. 36-37 illustrate another exemplary surgical system including a delivery device 382 and a staple 384. The delivery device 382 can be used for implanting staples 384 that do not have holes in their hinge regions 386. In an embodiment, the delivery device 382 engages the staple 384 underneath a staple bridge 388 and more specifically underneath each hinge region 386. The delivery device 382 may include pivot pins 390 that engage underneath the staple bridge 388. The pivot pins 390 are connected to pivot arms 392 that are pivotable relative to a body 394 of the delivery device 382.

Rotating a knob 396 (see FIG. 36) of the delivery device 382 causes a plunger 398 to deform the bridge 388 of the staple 384. In an embodiment, the plunger 398 includes a channel 397 sized to receive the bridge 388. In the deformed state, legs 399 of the staple 384 move toward a parallel position relative to one another for insertion into prepared bone holes. Turning the knob 396 counterclockwise releases the strain on the bridge 388 and allows the staple 384 to move back toward a convergent position.

Yet another surgical system is illustrated with respect to FIGS. 38-46. In this embodiment, the surgical system is a compression screw system for generating and applying compression within a body.

Figure 38:
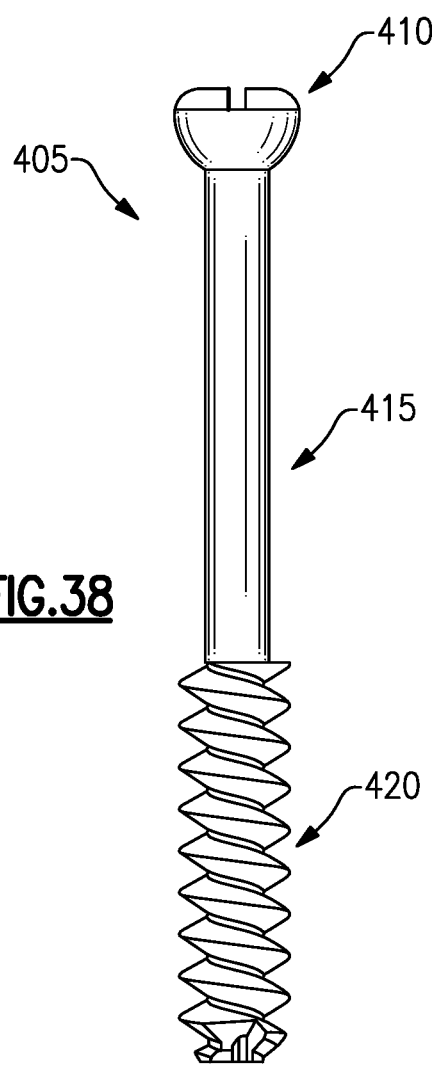
FIG. 38 is a schematic view of a novel compression screw formed in accordance with an embodiment of this disclosure.
Figure 39:
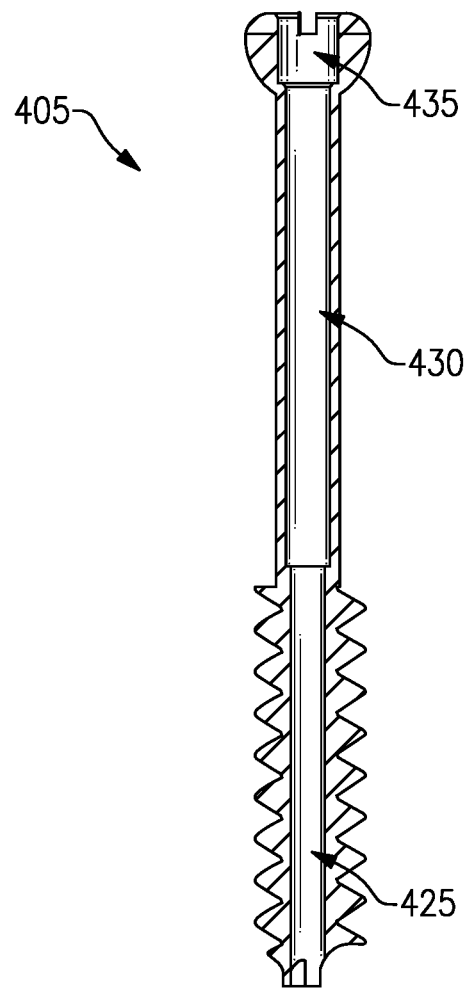
FIG. 39 is a schematic view of an interior of the novel compression screw of FIG. 36.

FIGS. 38-39 illustrate a compression screw 405 for bringing bones into close proximity with each other, generating a compressive load, and maintaining that compressive load for a prolonged period of time while the bone fuses. The compression screw 405 generally includes an enlarged proximal head 410, a reversibly axially strainable central region 415, and a distal threaded region 420. The compression screw 405 contains a central lumen 425 that extends the length of the compression screw 405 and a wider intermediate counterbore 430. The enlarged head 410 has an internally threaded region 435 for mating with an internal retaining pin.

Figure 40:
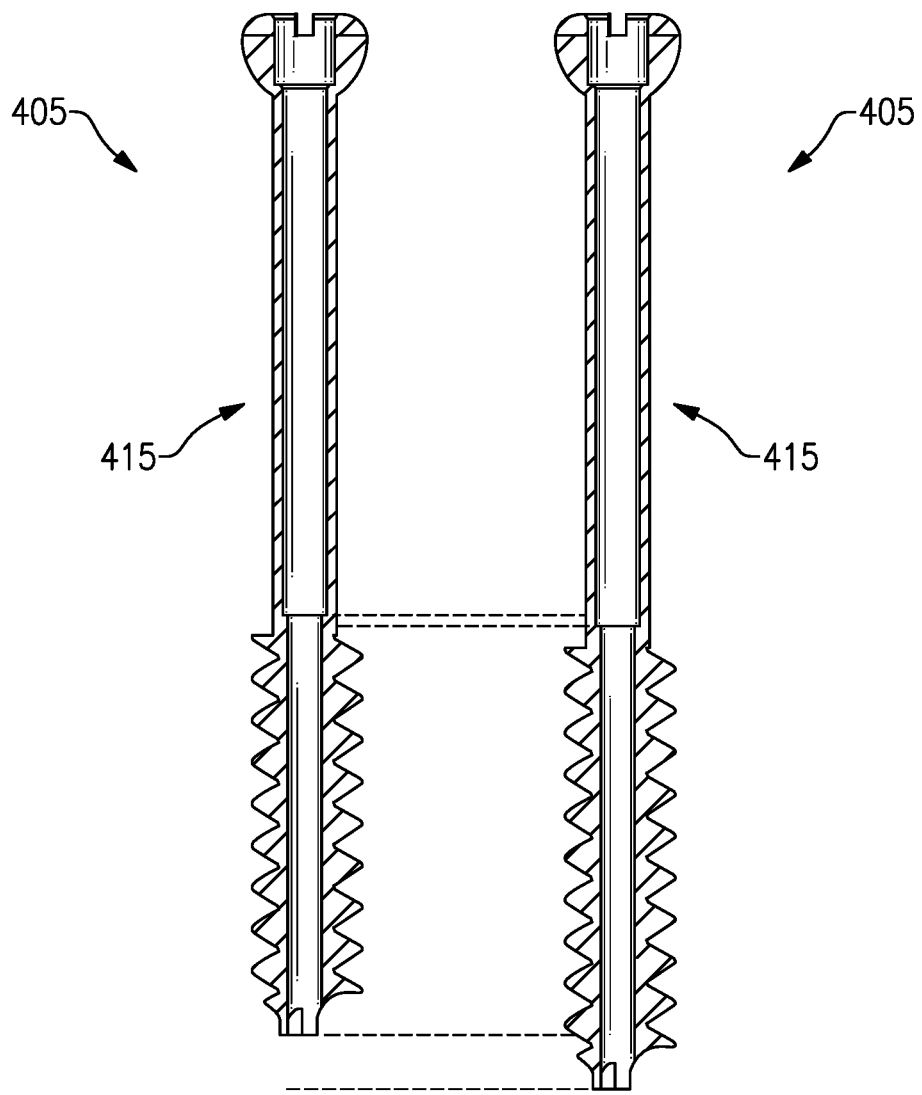
FIG. 40 is a schematic view showing how a central shaft region of the novel compression screw of FIG. 38 can be reversible stretched.

FIG. 40 schematically illustrates how the central region 415 of the compression screw 405 can be reversibly stretched. When the compression screw 405 is made from Nitinol, for example, that stretch can be up to 8%.

Figure 41:
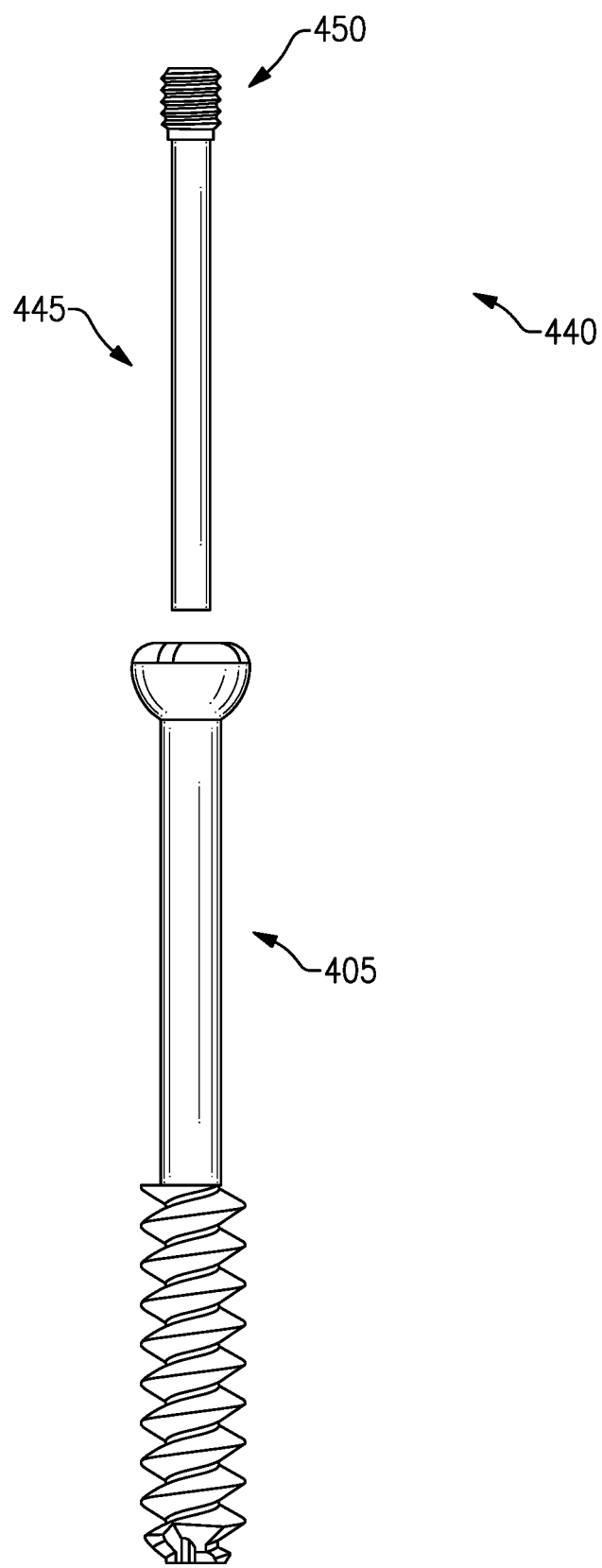
FIG. 41 illustrates a compression screw system including a screw and an internal retaining pin.
Figure 42:
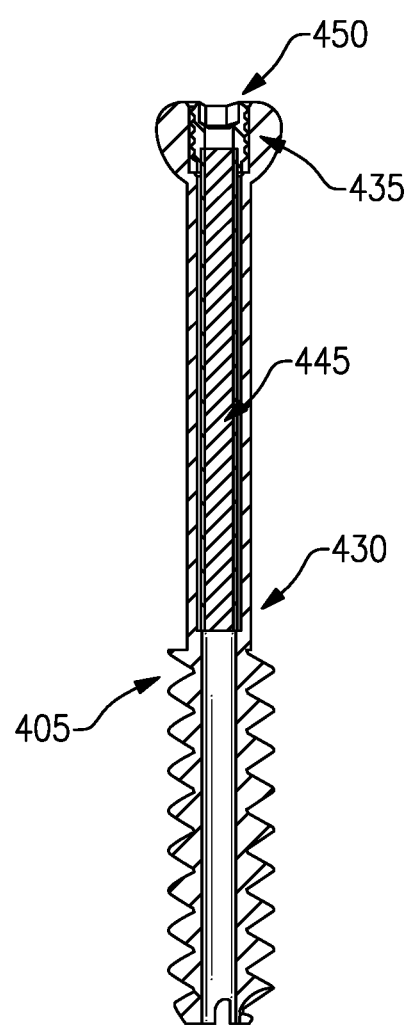
FIG. 42 illustrates the compression screw system with the internal retaining pin inserted within the screw to stretch and maintain the screw in an elongated state.

Referring to FIGS. 41-42, the surgical system includes a compression screw 405 and internal retaining pin 440. The internal retaining pin 440 comprises a tube 445 that is sized to slide into the intermediate counterbore 430 and a proximal threaded region 450 that mates with screw internal threaded region 435. When the screw 405 is stretched and the internal retaining pin 440 is inserted into the compression screw 405, the internal retaining pin 440 maintains the screw 405 in the elongated state. Removal of the internal retaining pin 440 allows the screw 405 to return to its original unstrained state.

Figure 43:
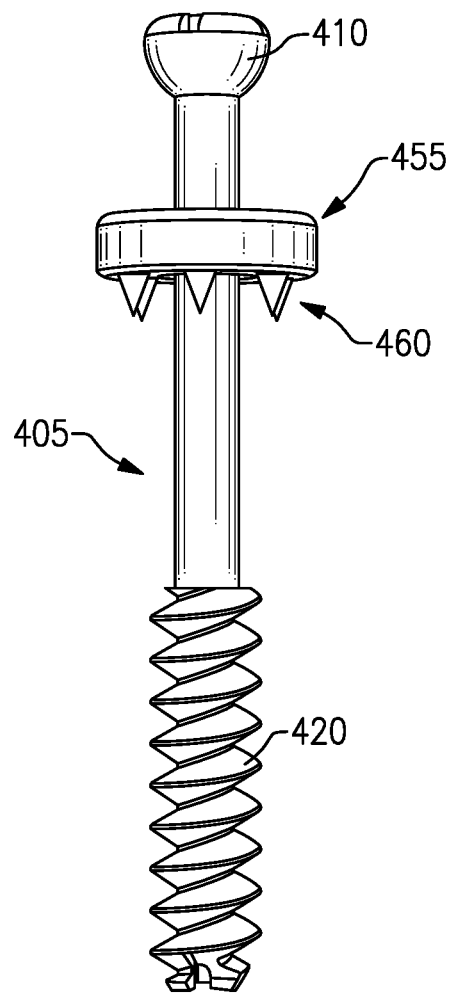
FIGS. 43, 44, and 45 schematically illustrate a compression screw system that includes a compression screw and a washer.
Figure 44:
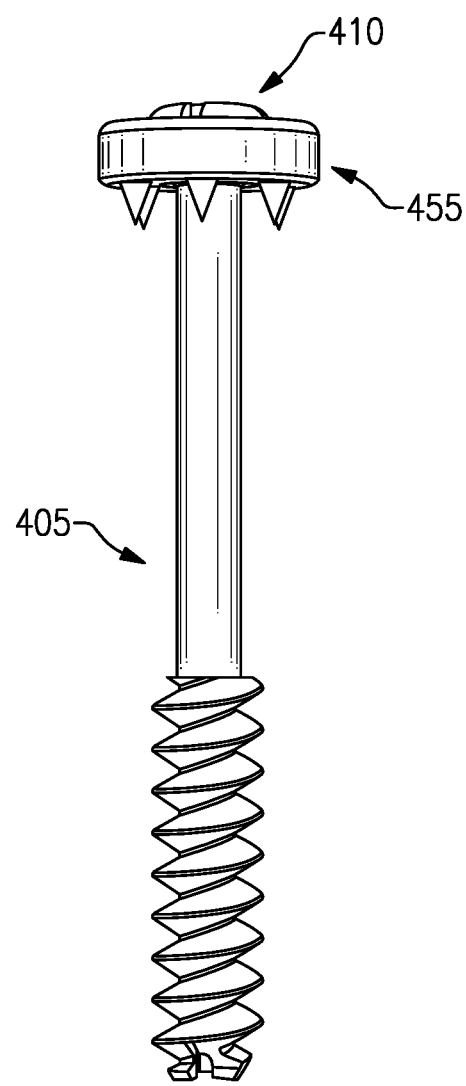
Figure 45:
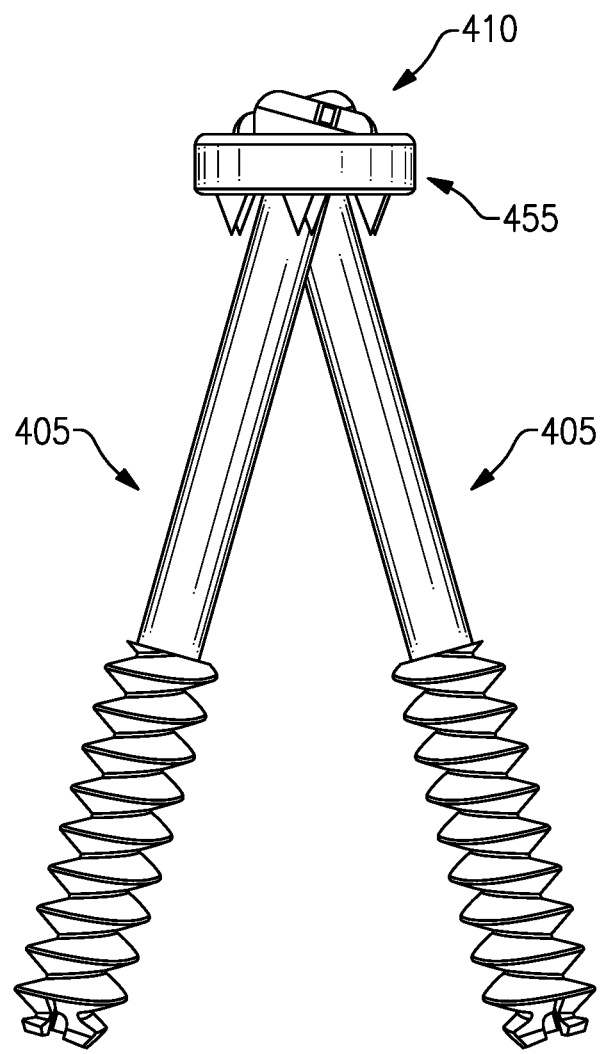

FIGS. 42-44 illustrate additional components of the surgical system. In an embodiment, the surgical system includes a washer 455. The washer 455 is sized to allow the distal threads 420 of the compression screw 405 to pass through the washer 455 but not allow enlarged head 410 to pass through. The washer 455 may have textured surface 460 on its distal face to better engage bone. The textured surface 460 may include spikes, in an embodiment. The washer 455 is designed to distribute the compressive load over a larger surface area. The washer 455 is contoured to allow the enlarged head 410 to articulate in the washer 455. This allows the screw 405 to be inserted at an angle (see, e.g., FIG. 45), and still have the washer 455 maximize its surface contact with the bone.

Figure 46:
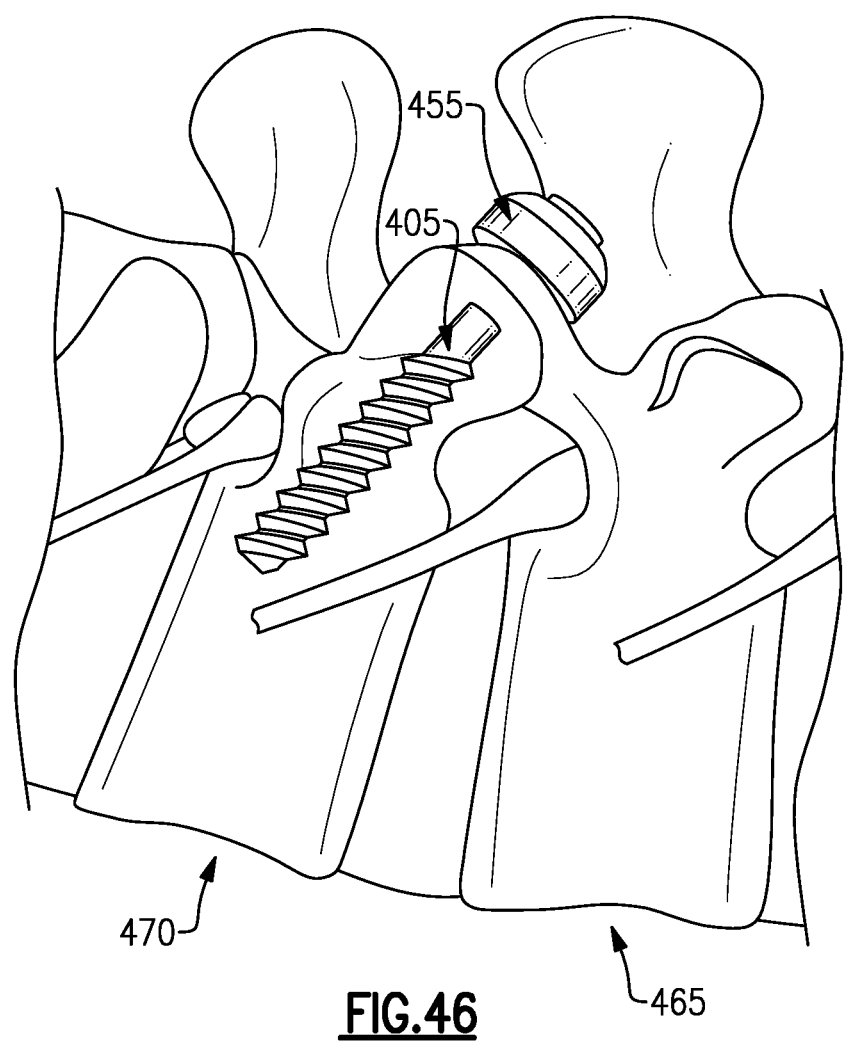
FIG. 46 is a schematic view showing a compression screw system being used to fuse adjacent vertebrae.

FIG. 46 shows the compression screw 405 and washer 455 being used to fuse two adjacent vertebra 465 and 470, such during a spinal fusion procedure.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical system comprising:
a staple mountable to a delivery device, the staple including a bridge, a first leg connected to the bridge by a first hinge region, and a second leg connected to the bridge by a second hinge region, wherein the staple is moveable between a first staple position and a second staple position; and
a delivery device including a staple mount including a channel that receives the bridge of the staple and a first arm and a second arm each pivotally connected at a pivot pin, wherein the delivery device is moveable between a first delivery device position where the staple is in the first staple position and a second delivery device position where the staple is in the second staple position, the first arm and the second arm include a first handle and a second handle, respectively, on one end of the first arm and the second arm, respectively, for actuating the delivery device, and the first arm and the second arm include a first stretching linkage and a second stretching linkage, respectively, on the other end of the first arm and the second arm, respectively, that define the staple mount including a channel that receives the bridge of the staple, wherein the staple mount includes a first stretching linkage having a first radii and including a first channel and a first pin and a second stretching linkage having a second radii and including a second channel and a second pin,
wherein the bridge of the staple is positioned in the channel of the staple mount when the staple is in the first staple position and the delivery device is in the first delivery device position,
wherein the first stretching linkage is mounted to the first arm by the first pin and the second stretching linkage is mounted to the second arm by the second pin, the first pin is slidable in the second channel of the second stretching linkage and the second pin is slidable in the first channel of the first stretching linkage, and the first stretching linkage and the second stretching linkage are distal to the channel,
wherein the first radii of the first stretching linkage and the second radii of the second stretching linkage mate with the first hinge region and the second hinge region, respectively, of the staple when the first handle and the second handle are moved inwardly to strain the bridge of the staple to move the staple from the first staple position to the second staple position, when the staple is in the first staple position, the first leg and the second leg of the staple are convergent, and when the staple is in the second staple position, the first leg and the second leg are substantially parallel to each other and substantially perpendicular to the bridge, and
wherein as the delivery devices moves from the first delivery device position and the second delivery device position, the first handle and the second handle move inwardly and the first stretching linkage and the second stretching linkage move outwardly, and
a locking feature that holds the staple in the second staple position.

2. The surgical system as recited in claim 1 wherein the delivery device includes a first outboard constraint and a second outboard constraint positioned outwardly from the first staple mount and the second staple mount, respectively, that prevents the first leg and the second leg of the staple from bending more than 90° when the staple moves from the first staple position to the second staple position, the first hinge of the staple is positioned between the first staple mount and the first outboard constraint, and the second hinge of the staple is positioned between the second staple mount and the second outboard constraint.

3. The surgical system as recited in claim 1 wherein the staple is made of a shape memory material.

4. The surgical system as recited in claim 3 wherein the staple is made of Nitinol.

5. A surgical system comprising:
a delivery device including a staple mount including a channel, the delivery device including a first arm and a second arm each pivotally connected at a pivot pin, wherein the first arm and the second arm have a first handle and a second handle, respectively, on one end of the first arm and the second arm, respectively, for actuating the delivery device, and the first arm and the second arm include a first stretching linkage and a second stretching linkage, respectively, on the other end of the first arm and the second arm for holding and straining a staple, wherein the delivery device is moveable between a first delivery device position and a second delivery device position; and
the staple mountable to the delivery device, the staple including a bridge, a first leg connected to the bridge by a first hinge region, and a second leg connected to the bridge by a second hinge region, wherein the staple is moveable between a first staple position and a second staple position, and the channel of the staple mount receives the bridge of the staple, and wherein the first handle and the second handle are moveable toward one another to translate the staple mount apart to strain the bridge to move the staple from the first staple position in which the first leg and the second leg are convergent and the second staple position in which the first leg and the second leg are substantially parallel to each other and substantially perpendicular to the bridge, wherein the first handle and the second handle are moved inwardly to strain the bridge of the staple to move the staple from the first staple position to the second staple position, the staple is in the first staple position when the first leg and the second leg of the staple are convergent, and the staple is in the second staple position when the first leg and the second leg are substantially parallel to each other and substantially perpendicular to the bridge.

6. The surgical system as recited in claim 5 wherein the delivery device includes a locking feature that holds the staple in the second staple position.

7. The surgical system as recited in claim 5 wherein the first stretching linkage and the second stretch linkage are distal to the channel, and a first radii of the first stretching linkage and a second radii of the second stretching linkage mate with the first hinge region and the second hinge region, respectively, of the staple when the first handle and the second handle are moved inwardly to strain the bridge in the channel of the staple mount to move the staple from the first staple position to the second staple position.

8. The surgical system as recited in claim 7 wherein the delivery device includes a first pin and a second pin, and the first stretching linkage and the second stretch linkage are mounted to the first arm and the second arm, respectively, by the first pin and the second pin, respectively.

9. The surgical system as recited in claim 8 wherein the first stretching linkage and the second stretching linkage include a first channel and a second channel, respectively, and the first pin and the second pin are mounted to the first stretching linkage and the second stretching linkage, respectively, and slide in the second channel of the second stretching linkage and the first channel of the first stretching linkage, respectively.

10. The surgical system as recited in claim 8 wherein the delivery device includes a first outboard constraint and a second outboard constraint positioned outwardly from the first staple mount and the second staple mount, respectively, that prevents the first leg and the second leg of the staple from bending more than 90° when the staple moves from the first staple position to the second staple position, the first hinge of the staple is positioned between the first staple mount and the first outboard constraint, and the second hinge of the staple is positioned between the second staple mount and the second outboard constraint.

11. The surgical system as recited in claim 5 wherein the delivery device is moveable between the first delivery device position where the staple is in the first staple position and the second delivery device position where the staple is in the second staple position, and when the delivery devices moves from the first delivery device position and the second delivery device position, the first handle and the second handle of the delivery device move inwardly and the first stretching linkage and the second stretching linkage move outwardly, respectively.

12. The surgical system as recited in claim 11 wherein the bridge of the staple is loaded onto the staple mount and positioned in the channel of the delivery device when the staple is in the first staple position and the delivery device is in the first delivery device position.

13. The surgical system as recited in claim 5 wherein the staple is made of a shape memory material.

14. The surgical system as recited in claim 13 wherein the staple is made of Nitinol.

* * * * *